(12) United States Patent
Tsuji et al.

(10) Patent No.: US 7,420,029 B2
(45) Date of Patent: Sep. 2, 2008

(54) TISSUE-SPECIFIC TRANSPORTER INHIBITOR

(75) Inventors: Akira Tsuji, Kanazawa (JP); Ikumi Tamai, Kanazawa (JP); Yoshimichi Sai, Kanazawa (JP); Noubuhiko Yui, Ishikawa (JP); Toru Oya, Ishikawa (JP); Ken-ichi Miyamoto, Tokushima (JP)

(73) Assignee: Japan Science and Technology Agency, Saitama (JP)

( * ) Notice: Subject to any disclaimer, the term of this patent is extended or adjusted under 35 U.S.C. 154(b) by 451 days.

(21) Appl. No.: 10/742,335

(22) Filed: Dec. 19, 2003

(65) Prior Publication Data

US 2004/0191211 A1    Sep. 30, 2004

Related U.S. Application Data

(63) Continuation-in-part of application No. PCT/JP02/06104, filed on Jun. 19, 2002.

(30) Foreign Application Priority Data

Jun. 21, 2001    (JP) .............................. 2001-188843

(51) Int. Cl.
*C07K 17/00* (2006.01)
*A61K 31/74* (2006.01)
*C07H 1/00* (2006.01)

(52) U.S. Cl. ................. 530/300; 424/78.08; 424/78.18; 424/78.19; 536/1.11

(58) Field of Classification Search ...................... None
See application file for complete search history.

(56) References Cited

FOREIGN PATENT DOCUMENTS

WO    WO 98/07449    2/1998

OTHER PUBLICATIONS

Inui et al., Physiological and pharmalogical implications of peptide transporters, PEPT1 and PEPT2, 2000, Nephrology Dialysis Transplant, vol. 15, Suppl 6, pp. 11-13.*
Takahashi et al., Upregulation of H+-peptide cotransporter PEPT2 in rat remnant kidney, 2001, American Journal Physiology Renal Physiology, vol. 281, pp. F1109-F1116.*
Tooru Ooya, et al., New Concept Of Multivalent Ligands: Polyrotaxane-Dipeptide Conjugates As A Specific Inhibitor Of Intestinal Peptide Transporter Pept1, Polymer Preprints, 2001, 42(2), p. 135-136.
Tami, Ikumi, Membrane Transporters As Determinant Of Drug Absorption And Disposition, (Abstract), Yakubutsu Dotai, 1996, 11(6), p. 642-650.
I. Tamai, et al., Retardation Of Progressive Chronic Renal Disease By Polyrotaxane-Dipeptide Conjugate That Inhibits Intestinal Peptide Transporter Pept1, Proceedings Int'l Symp. Control Rel. Bioact. Mater., 2001, 28, p. 1275-1276.

Nobuhiko Yui, et al., Inhibitory Effect Of Supramolecular Polyrotaxane-Dipeptide Conjugates On Digested Peptide Uptake Via Intestinal Human Peptide Transporter, Bioconjugate Chem., 2002, 13, p. 582-587.
Tooru Ooya, et al., New Concepts Of Multivalent Ligands; Polyrotaxane-Dipeptide Conjugates As A Specific Inhibitor Of Intestinal Peptide Transporter Pept1, (Abstract), $222^{ND}$ ACS National Meeting, American Chemical Society, Chicago IL, Aug. 26-30, 2001.
N. Najwa et al., "New Molecular Targets for Cholesterol-Lowering Therapy", J. Pharmacol. Exp. Ther., vol. 293, No. 2, pp. 315-320, Feb. 1, 2000.
Shimizu et al. Am J Physiol Gastrointest Liver Physiol. 288: G664-670, 2005.
Ooya T, Yamashita A, Kurisawa M, Sugaya Y, Maruyama A, Yui N. Effects of polyrotaxane structure on polyion complexation with DNA *Science and Technology of Advanced Materials* 5: 363-369, 2004.
Ooya, T, Eguchi M, Yui N. Supramolecular design for multivalent interaction: maltose mobility along polyrotaxane enhanced binding with concanavalin A. *Journal of American Chemical Society* 125: 13016-13017, 2003.
Ooya T, Choi HS, Yamashita A, Yui N, Sugaya Y, Kano A, Maruyama A, Akita H, Kogure K, Ito R, Harashima H. Biocleavable polyrotaxane-plasmid DNA polyplex for enhanced gene delivery. *Journal of American Chemical Society* 128: 3852-3853, 2006.
Eguchi M, Ooya T, Yui N. Controlling the mechanism of trypsin inhibition by the numbers of α-cyclodextrins and carboxyl groups in carboxyethylester-polyrotaxanes. *Journal of Controlled Release* 96: 301-307, 2004.
Yamashita A, Yui N, Ooya T, Kano A, Maruyama A, Akita H, Kogure K, Harashima H. Synthesis of a biocleavable polyrotaxane-plasmid DNA (pDNA) polyplex and its use for the rapid non-viral delivery of pDNA to cell nuclei. *Nature Protocol* 1: 2861-2869, 2007.
Ooya T, Utsunomiya H, Eguchi M, Yui N. Rapid binding of concanavalin A and maltose-polyrotaxane conjugates due to mobile motion of α-cyclodextrins threaded onto a poly(ethylene glycol). *Bioconjugate Chemistry* 16: 62-69, 2005.

* cited by examiner

*Primary Examiner*—Manjunath Rao
*Assistant Examiner*—Ian Dang
(74) *Attorney, Agent, or Firm*—Frommer Lawrence & Haug LLP; Thomas J. Kowalski; Russell A. Garman

(57) ABSTRACT

The present invention is to provide a tissue-specific transporter inhibitor which is not absorbed through the digestive tract and can prevent deterioration in the QOL of a patient caused by diet therapy, and a therapeutic drug for tissue dysfunction diseases and a therapeutic drug for suppressing the progress of chronic renal failure containing the inhibitor as an active ingredient. A tissue-specific transporter inhibitor which is not absorbed through the digestive tract is constructed by introducing a dipeptide which is a ligand of an oligopeptide transporter 1 into a supramolecular structure polyrotaxane wherein its structurally modified active residue is expected to be excellent in the interaction with a transmembrane transporter.

4 Claims, 13 Drawing Sheets

TISSUE-SPECIFIC TRANSPORTER INHIBITOR

REFERENCE TO RELATED APPLICATIONS

This application is a continuation-in-part of International Application PCT/JP02/06104 filed Jun. 19, 2002 and published as WO 03/000285 on Jan. 3, 2003, which claims priority from Japanese Application 2001-188843, filed Jun. 21, 2001.

Each of the applications and patents cited in this text, including each of the foregoing cited applications, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, various documents or references are cited in this text, either in a Reference List before the claims or in the text itself; and, each of the documents or references ("herein cited documents") and all of the documents cited in this text (also "herein cited documents"), as well as each document or reference cited in each of the herein cited documents (including any manufacturer's specifications, instructions, etc. for products mentioned herein and in any document incorporated herein by reference), is hereby expressly incorporated herein by reference. There is no admission that any of the various documents cited in this text are prior art as to the present invention. Also, teachings of herein cited documents and documents cited in herein cited documents and more generally in all documents incorporated herein by reference can be employed in the practice and utilities of the present invention.

FIELD OF THE INVENTION

The present invention relates to a tissue-specific transporter function inhibitor which has both a ligand structure recognized by a tissue-specific transporter and a polymeric molecular structure incapable of passing through a membrane tissue, and a therapeutic drug for tissue dysfunction diseases or a therapeutic drug for suppressing the progress of chronic renal failure containing the tissue-specific transporter function inhibitor as an active ingredient, and the like.

BACKGROUND

Nowadays, the number of dialysis patients are increasing, and it is presumed that the number of such patients will be enormous when taking into account the number of diabetic patients who will be in need of dialysis in the future, and the medical expenses for dialysis is estimated to be well over 1 trillion yen. Considering these situations, preventive medicine that prevents the onset of renal diseases and conservative treatments that prevent the progress of renal failure into dialysis are regarded important. Effective treatments of renal disorders in patients of chronic renal failure have not been established yet, treatments including low protein diet therapy and the administration of antihypertensive drugs such as an ACE inhibitor have been conducted so far (Am. J. Cardiol. 59, 66A-71A, 1987; Am. J. Kidney. 20, 443-57, 1992; BMJ 304, 216-20, 1992; Ann. Intern. Med. 124, 627-32, 1996). The above-mentioned low protein diet therapy is thought to be effective means to suppress the progress of chronic renal failure and is widely conducted currently. However, since dietary restriction contains problems of quality of life (QOL) and compliance of patients, a new therapeutic strategy, for example, suppression of oral protein absorption, is needed. Recently, as a new strategy for the treatment of hyperlipemia, it is reported that biosynthesis of cholesterol is suppressed by inhibiting a bile acid transporter present in the small intestine, and this report draws attention (J. Pharmacol. Exp. Ther. 293, 315-20 2000). Likewise, it is expected that the absorption of proteins through the digestive tract can be suppressed by a specific inhibitor.

The present inventors have reported that proteins taken are digested in the digestive tract to amino acids and oligopeptides and absorbed through the small intestine, and that the absorption is conducted by a specific transporter present in the brush border membrane of a small intestine epithelial cell (Pharm. Res. 13, 963-77, 1996). The digested amino acids mentioned above are transported by multiple transporters, however, the oligopeptides are transported by an oligopeptide transporter such as PEPT 1, and absorbed dipeptide- or tripeptide-specifically (J. Biol. Chem. 270, 6456-63, 1995). As to the absorption of digestive products of proteins in the small intestine, it is known that more peptides are absorbed than amino acids (Gastroenterology 113, 332-40, 1997). Taken together, it is considered that a PEPT 1 inhibitor is capable of suppressing the absorption of proteins in the diet, and is useful for the patients whose QOL is deteriorated due to diet therapy.

Since 1994, PEPT 1 genes have been cloned from small intestines of rabbit, human and rat (J. Biol. Chem. 270, 6456-63, 1995; Nature 368, 563-6, 1994; J. Pharma. Exp. Ther. 275, 1631-7, 1995; Biochim. Biophys. Acta, 1305, 34-8, 1996), and studies for transportation via PEPT 1 have been rapidly developed. The above-mentioned PEPT 1 gene derived from rat small intestine has been cloned for the first time by the present inventors (Biochim. Biophys. Acta, 1305, 34-8, 1996), and revealed to locate in the brush border membrane side of the small intestine epithelial cell by immunohistochemical technique (FEBS Lett. 392, 25-9, 1996). In addition, it is reported that PEPT 1 recognizes and transports compounds such as valacyclovir, an antiviral drug, that does not have a peptide bond in its molecules, as well as compounds having peptide-like structures, for example, β-lactam antibiotics (Pharm. Res. 13, 963-77, 1996; Biochem. Biophys. Res. Commun. 250, 246-51, 1998; J. Clin. Invest. 101, 2761-7, 1998; J. Biol. Chem. 273, 20-2, 1998). As mentioned above, PEPT 1 shows wide range of substrate recognition property, however, its molecular recognition property remains unknown and it is thought that the substrate recognition of PEPT 1 involves not only the recognition of partial structure but also whole molecule. Meanwhile, PEPT 2, which is cloned from the kidney (Biochim. Biophys. Acta, 1235, 461-6, 1995; Biochim. Biophys. Acta, 1280, 173-7, 1996; Proc. Natl. Acad. Sci. USA 93, 284-9, 1996), locates in the brush border membrane side of the epithelial cell in the proximal convoluted tubule of the kidney, and has a substrate recognition property similar to that of PEPT 1, and serves to reabsorbing oligopeptides and peptide-like compounds. The above-mentioned PEPT 1 is known to express in the kidney though it does not contribute very much (Am. J. Physiol. 276, F658-65, 1999). However, PEPT 2 has never been observed to express in the small intestine.

In human, it is reported that bioavailability (BA) of cefadroxil (CDX), a β-lactam antibiotic and a substrate of PEPT 1, is decreased by co administration of cephalexin (CEX), a β-lactam antibiotic similarly recognized by PEPT 1 (Eur. J. Clin. Pharmacol. 41, 179-83, 1991). A mechanism in which AUC (Area Under the plasma concentration Curve) as an index of bioavailability is decreased by CEX includes both the absorption of CDX in the small intestine and the inhibition of reabsorption of CDX in the kidney. The reabsorption through the kidney is conducted mainly via an oligopeptide transporter (PEPT 2), and both compounds are known to be substrates for PEPT 2 (Biochim. Biophys. Acta, 1235, 461-6, 1995). Therefore, it is explicable that the decrease of BA of CDX caused by CEX means that CDX transportation via PEPT 1 and PEPT 2 is inhibited by CEX. Though the effect of the inhibition of PEPT 2 present in the kidney on a living organism is unknown, it seems preferable to limit to a direct inhibition of absorption via PEPT 1 from the viewpoint of diet therapy for chronic renal failure. However, since PEPT 1 and PEPT 2 show very similar substrate recognition properties, it has been presumed to be difficult to develop an inhibitor which specifically recognizes PEPT 1.

The number of dialysis patients due to renal failure are increasing, and it is presumed that the number of such patients will be enormous when taking into account the number of diabetic patients who will be in need of dialysis, and the medical expenses for dialysis is estimated to be well over 1 trillion yen in the future. Under these circumstances, preventive medicine that prevents the onset of renal diseases and conservative treatments that prevent the progress of renal failure into dialysis are important. The object of the present invention is to provide a tissue-specific transporter inhibitor which is not absorbed through the digestive tract and can prevent deterioration in the QOL of patients caused by diet therapy, and a therapeutic drug for tissue dysfunction diseases and a therapeutic drug for suppressing the progress of chronic renal failure containing the inhibitor as an active ingredient.

The present inventors have considered that it is effective to use a PEPT 1 inhibitor which is not absorbed through the digestive tract and is able to avoid recognizing PEPT 2 in order to attain the above-mentioned object, and that PEPT 1 can be selectively inhibited by designing a polymer compound having PEPT 1 recognition property because polymer compounds are not absorbed through the digestive tract in general. Therefore, the present inventors have focused on a supramolecular structure polyrotaxane (PRX) wherein its structurally modified active residue is expected to be excellent in the interaction with a transmembrane transporter, and constructed a compound wherein a dipeptide (Val-Lys) which is a ligand of the PEPT 1 mentioned above is introduced into a supramolecular structure PRX. As a result of intensive study, it has been found that the above-mentioned compound can suppress the absorption of proteins and the progress of chronic renal failure which needs limitation of protein uptake, and thus the present invention has been completed.

BRIEF DESCRIPTION OF THE INVENTION

The present invention relates to a tissue-specific transporter function inhibitor which has both a ligand structure recognized by a tissue-specific transporter and a polymeric molecular structure incapable of passing through a membrane tissue (paragraph 1), the tissue-specific transporter function inhibitor according to paragraph 1, wherein the polymeric molecular structure incapable of passing through a membrane tissue is a supramolecular structure (paragraph 2), the tissue-specific transporter function inhibitor according to paragraph 2, wherein the supramolecular structure is a rotaxane compound in which a number of circular molecules are penetrated by linear molecules, and both ends of the linear molecules are capped by bulky substituents (paragraph 3), the tissue-specific transporter function inhibitor according to paragraph 3, wherein the circular molecules are cyclodextrins (paragraph 4), the tissue-specific transporter function inhibitor according to paragraph 3 or 4, wherein the linear molecules are polyethyleneglycols (paragraph 5), the tissue-specific transporter function inhibitor according to any one of paragraphs 3 to 5, wherein the bulky substituents are N-benzyloxycarbonyl-L-phenylalanines (paragraph 6), the tissue-specific transporter function inhibitor according to paragraph 1, wherein the polymeric molecular structure incapable of passing through a membrane tissue is an α-cyclodextrin structure (paragraph 7), the tissue-specific transporter function inhibitor according to any one of paragraphs 1 to 7, wherein the ligand recognized by a tissue-specific transporter is an organic anionic substance, an organic cationic substance, or a peptidergic substance (paragraph 8), the tissue-specific transporter function inhibitor according to any one of paragraphs 1 to 8, wherein the tissue-specific transporter is a small intestine-specific transporter (paragraph 9), the tissue-specific transporter function inhibitor according to paragraph 9, wherein the small intestine-specific transporter is an oligopeptide transporter 1 (PEPT 1) (paragraph 10), and the tissue-specific transporter function inhibitor according to paragraph 10, wherein a peptidergic substance recognized by the oligopeptide transporter 1 (PEPT 1) is valyl-lysine (Val-Lys) (paragraph 11).

The present invention also relates to a therapeutic drug for tissue dysfunction diseases which contains the tissue-specific transporter function inhibitor according to any one of paragraphs 1 to 11 as an active ingredient (paragraph 12), and a therapeutic drug for suppressing the progress of chronic renal failure which contains the tissue-specific transporter function inhibitor according to any one of paragraphs 1 to 11 as an active ingredient, wherein the inhibitor is a protein absorption inhibitor (paragraph 13).

DETAILED DESCRIPTION OF THE INVENTION

Figure 1:
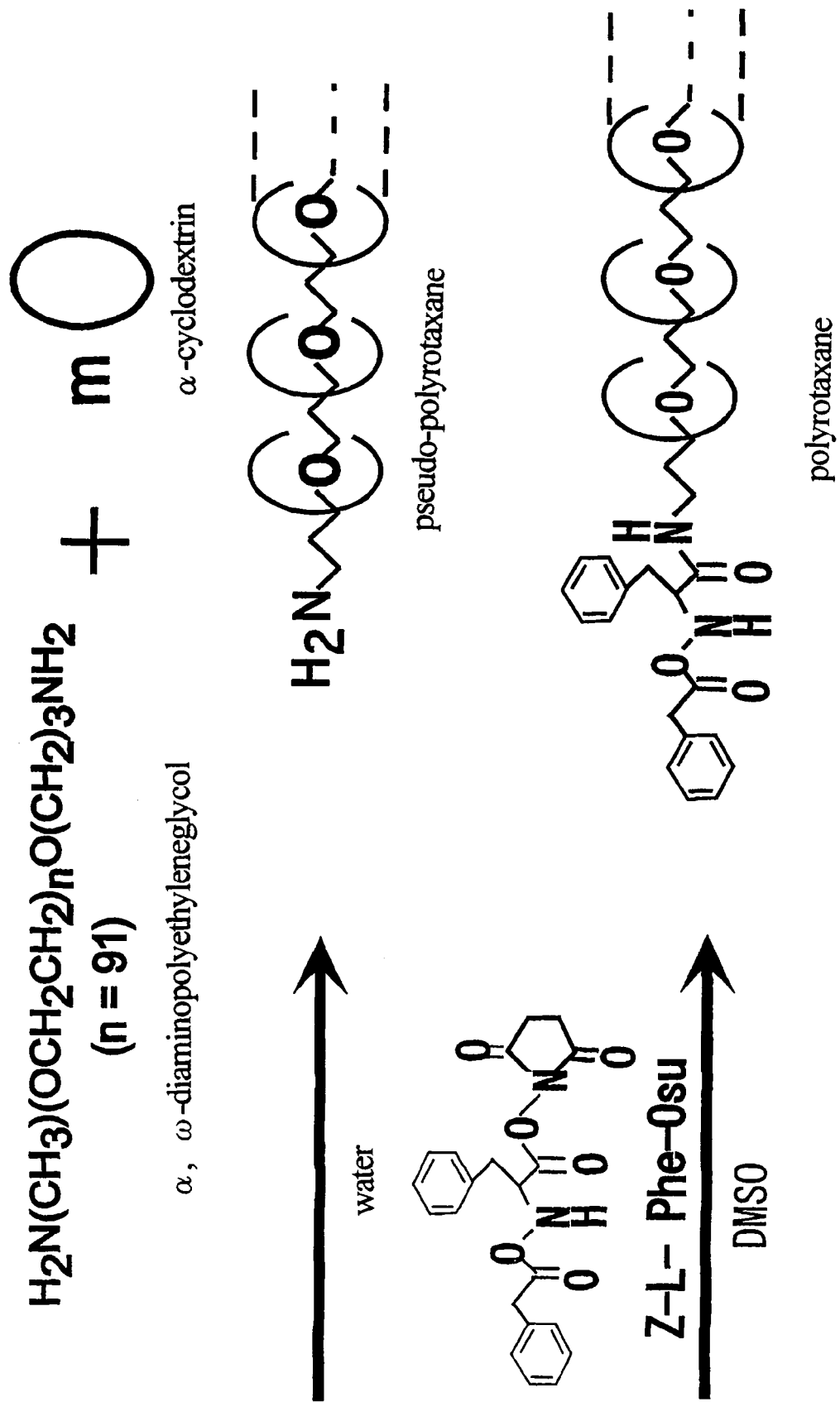
FIG. 1 is a schema showing the synthetic procedure of polyrotaxane.

As a tissue-specific transporter function inhibitor according to the present invention, any substance can be used as long as it has a ligand structure recognized by a tissue-specific transporter and a polymeric molecular structure incapable of passing through a membrane tissue, and inhibits the function of the above-mentioned tissue-specific transporter, however, those that have physiologically stable structures are preferable. Examples of the tissue include; small intestine, kidney, brain, liver, placenta, pancreas, lung, stomach, ovary, testis, spleen, large intestine, skeletal muscle, airway, bone marrow, prostate gland, heart, uterus, spinal cord, adrenal gland, thyroid gland, etc., and specific examples of the transporters which specifically express in such tissue include, but not limited to, transporters shown in Tables 1 to 3.

TABLE 1

| Type | Name | Accession No. (GenBank, NCBI) | Reference (Journal, vol, pages, year) | Tissue Distribution | Substrate to be Transported |
|---|---|---|---|---|---|
| Organic anion transporter | OAT1 | AB004559 | J. Biol. Chem., 272, 18526-18529, 1997 | Kidney, (brain) | β-lactam antibiotics (Penicilline G, Cephaloridine), antiviral drugs (azidothymidine, acyclovir), nonsteroidal antiinflammatory drugs (salicylate, acetylsalicylate, indomethacin), ACE inhibitor (captopril), anticancer drug (methotrexate), metabolites (p-aminohippuric acid, uric acid), ochratoxin A, cAMP, cGMP |
| | OAT2 | NM_006672 | FEBS Lett., 429, 179-182, 1998 | Liver, kidney | salicylate, acetylsalicylate, p-aminohippuric acid, prostaglandin E2, etc. |
| | OAT3 | AB017446 | J. Biol. Chem., 274, 13675-13680, 1999 | Kidney, liver, brain | p-aminohippuric acid, ochratoxin A, estron sulfate conjugate, cimetidine, etc. |
| | OAT4 | | J. Biol. Chem., 275, 4507-4512, 2000 | Placenta, kidney | sulfic acid conjugates of various pharmaceuticals |
| Organic anion transporter | OATP-A | U21943 | Biochem. Biophys. Res. Commun., 273, 251-260, 2000 | Kidney, brain | |
| | OATP-B | AB026256 | Biochem. Biophys. Res. Commun., 273, 251-260, 2000 | Pancreas, liver, lung, intestinal tract, ovary, testis, spleen | Estron sulfate conjugate, prostaglandin E2 |
| | OATP-C/ LST1/ OATP-2 | AB026257 | Biochem. Biophys. Res. Commun., 273, 251-260, 2000 | Liver | Taurocholic acid, pravastatin, dehydroepiandrosterone sulfate conjugate, estradiol glucuronate conjugate, prostaglandin E2, thromboxane B2, leukotoriene B2, etc. |
| | OATP-D | AB031050 | Biochem. Biophys. Res. Commun., 273, 251-260, 2000 | Most of normal tissues and cancer cells | Estron sulfate conjugate, prostaglandin E2 |
| | OATP-E | AB031051 | Biochem. Biophys. Res. Commun., 273, 251-260, 2000 | Most of normal tissues and cancer cells | Estron sulfate conjugate, prostaglandin E2 |
| | PGT | NM_005630 | Science, 268, 866-869, 1995 | Pancreas, lung, intestinal tract, ovary ovary | Prostaglandin (PGE2, PGF2u, D2), thromboxane B2, etc. |
| | oatp1 | AF148218 | Proc. Natl. Acad. Sci. USA, 91, 133-137, 1994 | Liver, kidney, large intestine, brain, lung, skeletal muscle | Organic acid (sulfate conjugate such as cholate, taurocholate, BSP, estron sulfate, digitoxin, ouabain, enalapril, temocaprilat, pravastatin, estron; glucuronate conjugate such as estradiol; leucotrien C4, ouabain, BQ-123, etc.). |
| | oatp2 | U88036 | Proc. Nat.l. Acad. Sci. USA, 94, 10346-10350, 1997 | Liver, kidney, brain | sulfate conjugate such as bile acid, pravastatin, estron; glucuronate conjugate such as estradiol; thyroid hormone, ouabain, digoxin, BQ-123, leuci-enkephalin, etc. |
| | oatp3 | U95001 | J. Biol. Chem., 273, 22395-22401, 1998 | Liver, brain | |
| | OAT-K1 | D79981 | J. Biol. Chem., 271, 20719-20725, 1996 | Kidney | |
| | Npt1 | X71355 | Genomics, 18, 255-359, 1993 | Kidney, liver | p-aminohippuric acid, β-lactam antibiotics (Penicilline G, faropenem, etc.), forcarnet, mevalonic acid |

TABLE 2

| Type | Name | Accession No. (GenBank, NCBI) | Reference (Journal, vol, pages, year) | Tissue Distribution | Substrate to be Transported |
|---|---|---|---|---|---|
| Monocarboxylic acid transporter | MCT1 | D63834 | Biochem. Biophys. Res. Commun., 217, 370-375, 1995 | Normal tissue of almost all over the body | Lactic acid, β-hydroxy butyrate, acetic acid, propionic acid |
| | AE2 | | | | Benzoic acid, nicotinic acid, propionic acid, butyric acid, valproic acid |
| Organic cation transporter | OCT1 | X78855 | Nature, 372, 549-552, 1994 | Liver, kidney, intestinal epithelial cell (blood vessel side) | Cholin, dopamine, adrenalin, tetraethyl ammonium, N-methylnicotinamide, cimetidine, amantadine. |
| | OCT2 | D83044 | Biochem. Biophys. Res. Commun., 224, 500-507, 1996 | Kidney, brain | |
| | OCT3 | AF055286 | J. Biol. Chem., 273, 15971-15979, 1998 | Kidney, brain, intestinal tract | |
| Organic cation transporter | OCTN1 | AB007448 AB016257 | FEBS Lett., 419, 107-111, 1998 | Kidney, airway, bone marrow, skeletal muscle, prostate gland, lung, pancreas, placenta, heart, uterus, spleen, spinal cord, many cancer cells | Tetraethyl ammonium, quinidine, pyrilamine, verapamil, carnitine |
| | OCTN2 | AB015050 AB015800 | J. Biol. Chem., 273, 20378-20382, 1998 Nature Genet. 21, 91-94 (1999) | Kidney, skeletal muscle, placenta, heart, small intestine, prostate gland, adrenal gland, airway, thyroid, many cancer cells | Carnitine, acetylcarnitine, pyrilamine, verapamil |
| | OCTN3 | NM_019723 | J. Biol. Chem., in press (Sep. 28, 2000) | | |
| Peptide transporter | PEPT1 | U13173 | J. Biol. Chem., 270, 6456-6463, 1995 Biochim. Biophys. Acta, 1305, 34-38, 1996 | Small intestine, kidney, cancer cell | Dipeptide, tripeptide, β-lactam antibiotics (cyclacillin, cephadroxil, cephalexin, cephradine, ceftibuten, etc.), ACE inhibitor (captopril), anticancer drug (bestatin), antiviral drug (valacyclovir) |
| | PEPT2 | D63149 | Biochim, Biophys, Acta, 1240, 1-4, 1995 | Kidney | Cefadroxil |

TABLE 3

| Type | Name | Accession No. (GenBank, NCBI) | Reference (Journal, vol, pages, year) | Tissue Distribution | Substrate to be Transported |
|---|---|---|---|---|---|
| Amino acid transporter | LAT1 | AB015432 | J. Biol. Chem., 273, 23629-23632, 1998 | | Neutral amino acid (leucine), amino acid analogues (T3, T4, L-dopa, gabapentin, merpharan) |
| | LAT2 | AF171669 | J. Biol. Chem., 274, 19745-19751, 1999 | Normal tissue of almost all over the body | |
| | BAT1 | AB029559 | J. Biol. Chem., 274, 28845-28848, 1999 | | |
| | Xc- | AB022345 | J. Biol. Chem., 274, 11455-11458, 1999 | | |
| | y + LAT1 | AJ130718 | Nature Genet, 21, 293-296, 1999 | | |
| | y + LAT2 asc1 | NM_012244 | EMBO J., 18, 49-57, 1999 J. Biol. Chem., 275, 9690-9698, 2000 | | |
| | MDR1 | M62425 | Cell, 47, 381-389, 1986 | | Anticancer drugs (daunorubicin, doxorubicine, etoposide, vinblastine, vincristine, mitomycin C, paclitaxel) Other pharmaceuticals (digoxin, progesterone, morphine, rifampicin, diltiazem, nifedipine, erythromycin) |
| | MRP1 | AJ277881 | Science, 258, 1650-1654, 1992 | Various cancers, kidney, liver, spleen, adrenal gland, lung, heart, skeletal muscle | |
| | MRP2 MRP3 | AF261713 AF009670 | Science, 271, 1126-1128, 1996 | Liver | Glutathione, various conjugates, methotrexate, pravastatin, temocaprilat, new quinolon antimicrobial |

As the above-mentioned polymeric molecular structure incapable of passing through a membrane tissue, any structure can be used as long as it is a polymeric structure incapable of or having difficulty in passing through a membrane tissue in a living organism, for example, a membrane tissue in small intestine, kidney, brain, liver, placenta, pancreas, lung, stomach, ovary, testis, spleen, large intestine, skeletal muscle, airway, bone marrow, prostate gland, heart, uterus, spinal cord, adrenal gland, thyroid gland, etc. The specific examples include a supramolecular structure such as a polyrotaxane compound in which a number of circular molecules are penetrated by linear molecules, and both ends of the linear molecules are capped by bulky substituents, and a derivative or a clathrate structure containing α-cyclodextrin. The specific examples of the circular molecules mentioned above include but not particularly limited to molecules such as cyclodextrin, α-, β-, or γ-cyclodextrin, crown ether, and cyclofructan. As the linear molecules, molecules such as polyethyleneglycol, polypropylene glycol, or copolymer of polyethyleneglycol and polypropylene glycol, polyamino acid, polysaccharides, etc. are exemplified, however, polyethyleneglycol and the like, to which a bulky substituent can be introduced, is preferable. The bulky substituent is not particularly limited as long as it can prevent desorption of the circular molecules mentioned above, and the specific examples include but not particularly limited to an oligopeptide comprising a unit or units of any one of N-benzyloxycarbonyl-L-phenylalanine, alanine, valine, leucine, isoleucine, methionine, proline, phenylalanine, tryptophan, aspartic acid, glutamic acid, glycine, serine, threonine, tyrosine, cysteine, lysine, arginine, histidine, or derivatives thereof.

The specific examples of the ligand recognized by a tissue-specific transporter in the present invention include an organic anionic substance, an organic cationic substance, a peptidergic substance and a substance having an amino group. For example, the specific examples of the ligand recognized by an oligopeptide transporter 1 (PEPT 1), a transporter that specifically expresses in the small intestine, include but not limited to oligopeptides such as a dipeptide and a tripeptide, derivatives thereof whose constitutive amino acid residues are modified, β-lactam antibiotics such as cefadroxil and ceftibuten, ACE inhibitors such as captopril, bestatin which is an anticancer drug, and valacyclovir which is an antiviral drug.

As a therapeutic drug for tissue dysfunction diseases provided by the present invention, a drug that contains the tissue-specific transporter function inhibitor as an active ingredient, and as a therapeutic drug for suppressing the progress of chronic renal failure provided by the present invention, a drug that contains the tissue-specific transporter function inhibitor that suppresses protein absorption as an active ingredient are exemplified respectively. It is preferable for the therapeutic drugs to have shapes capable of being administered orally, intravenously, intraperitoneally, intranasaly, intracutaneously, subcutaneously, intramuscularly, or in other such manners. It is possible to conveniently determine the effective amount of the drugs to be administered in consideration of the types and compositions of the drugs, its administration route, age and body weight of patients, etc., and it is preferable to administer the effective amount of the drugs one to a few times a day. Further, in the case of oral administration, the drugs are usually administered in a form of a drug prepared by mixing with carriers for formulation. As the carriers for drug formulation, substances which are conventionally used in the drug formulation field, and does not react with the tissue-specific transporter function inhibitor according to the present invention are used. The oral administration of the drugs can be conducted at each meal, or before each meal.

In addition, specific examples of dosage forms include tablets, capsules, granules, powders, syrups, suspensions, suppositories, ointments, creams, gels, transdermal preparations, respiratory tonics, injectable solutions. These drugs are prepared according to conventional methods, and liquid drugs, in particular, can be prepared also in a form that can be dissolved or suspended in water or other suitable media before use. Tablets and granules may be coated by known methods. The injectable solutions are prepared by dissolving the peptide-modified polymers of the present invention into water, however, if necessary, instead of water, saline or glucose solution may be used for dissolution, and buffers or preservatives may be added. These drugs may contain other therapeutically valuable components.

It is also possible to blend the tissue-specific transporter function inhibitor of the present invention, as a food material for ameliorating the symptoms of tissue dysfunction diseases or chronic renal failure, into foods and to take such foods as functional foods. The examples of such foods are: bread and confectionery including baked goods such as puddings, cookies, bread, cakes, jellies, rice crackers, Japanese sweets such as "yokan" (a sweet jelly made from bean jam), frozen desserts, chewing gums; noodles such as wheat noodles and buck wheat noodles; fish paste products such as steamed fish paste, fish ham, fish sausages; various beverages such as yogurt, yogurt drinks, juice, milk, soy milk, alcoholic drinks, coffee, tea, green tea, oolong tea, isotonic drinks; seasonings such as miso, soy sauce, dressings, mayonnaise, sweeteners; various delicatessen such as tofu, devil's tongue, "tsukudani" (fish boiled on soy sauce), jiao-zi, croquettes, salad, etc.

EXAMPLES

Hereinafter, preferred examples of the present invention are described, however, the present invention is not limited to these examples.

Example 1

[Synthesis of Polyrotaxane (PRX); see FIG. 1]

1-1 (Preparation of Pseudo-polyrotaxane Comprised of Polyethyleneglycol and α-cyclodextrin)

An aqueous solution (9.14 g/85 ml) of polyethyleneglycol (PEG-BA, Mn=4000) whose both ends were aminated was dropped into α-cyclodextrin (α-CD) saturated aqueous solution (100 g/600 ml), which was being sonicated during the dropping. The resultant solution was sonicated and stirred for about one hour, and left overnight. Then, centrifugation was performed, and precipitate was collected and dried under reduced pressure at 60° C. Thus, 78.13 g of pseudo-polyrotaxane, a linear molecule wherein polyethyleneglycol (PEG) was penetrating into cyclodextrin was prepared.

1-2 (Preparation of an End-cap Agent)

In order to introduce N-benzyloxycarbonyl-L-phenylalanine (Z-L-Phe, Z represents a benzyloxycarbonyl group) as a bulky substituent that prevents the desorption of α-CD, a carboxyl group in Z-L-Phe was activated. 38.46 g (0.33 mol) of N-hydroxysuccinimide (HOSu) and 100 g (0.33 mol) of Z-L-Phe were dissolved in 850 ml of dioxane. Next, 68.90 g (0.33 mol) of ice-cooled N,N'-dicyclohexylcarbodiimide (DCC) was added and the resultant solution was stirred for about one hour, and subsequently, left overnight in a refrigerator. After removing the precipitate formed, its supernatant was concentrated under reduced pressure and the obtained concentrated solution was re-precipitated in diethyl ether. The precipitate formed was dried under reduced pressure at ambient temperature and collected, and re-crystallized with dichloromethane and petroleum ether. Then, the sample was filtrated and dried under reduced pressure, and 105.84 g (0.26 mol) of succinimide ester of Z-L-Phe (Z-L-Phe-OSu), a white needle crystal, was obtained.

1-3 (Synthesis of Polyrotaxane Using Z-L-Phe-OSu)

24.3 g (0.68 mmol) of pseudo-polyrotaxane obtaind in Example 1-1, and 28.8 g (72 mmol) of Z-L-Phe-OSu obtaind in Example 1-2 were added to 30 ml of dimethyl sulfoxide, and the resultant solution was stirred for about 4.5 days in heterogeneous condition. In the procedure, the molar ratio of Z-L-Phe-OSu (—OSu) to a terminal amino group of pseudo-polyrotaxane (—NH$_2$) was 50:1. After the reaction, the above solution was poured into a large amount of ether, and the resultant white precipitate was dried under reduced pressure and collected. In order to remove Z-L-Phe-OSu, α-CD, and PEG-BA that were not reacted, the precipitate was washed three times each with acetone and water. Finally the obtained sample was dried under reduced pressure at 60° C., and 13 g of polyrotaxane (white powder), wherein both ends of pseudo-polyrotaxane were capped by bulky substituents, was obtained. The structural analysis of the synthesized polyrotaxane was performed by $^1$HNMR spectral measurement (Varian; 300 MHz FT-NMR).

Example 2

[Synthesis of a Dipeptide Recognized by a Peptide Transporter]

Figure 2:
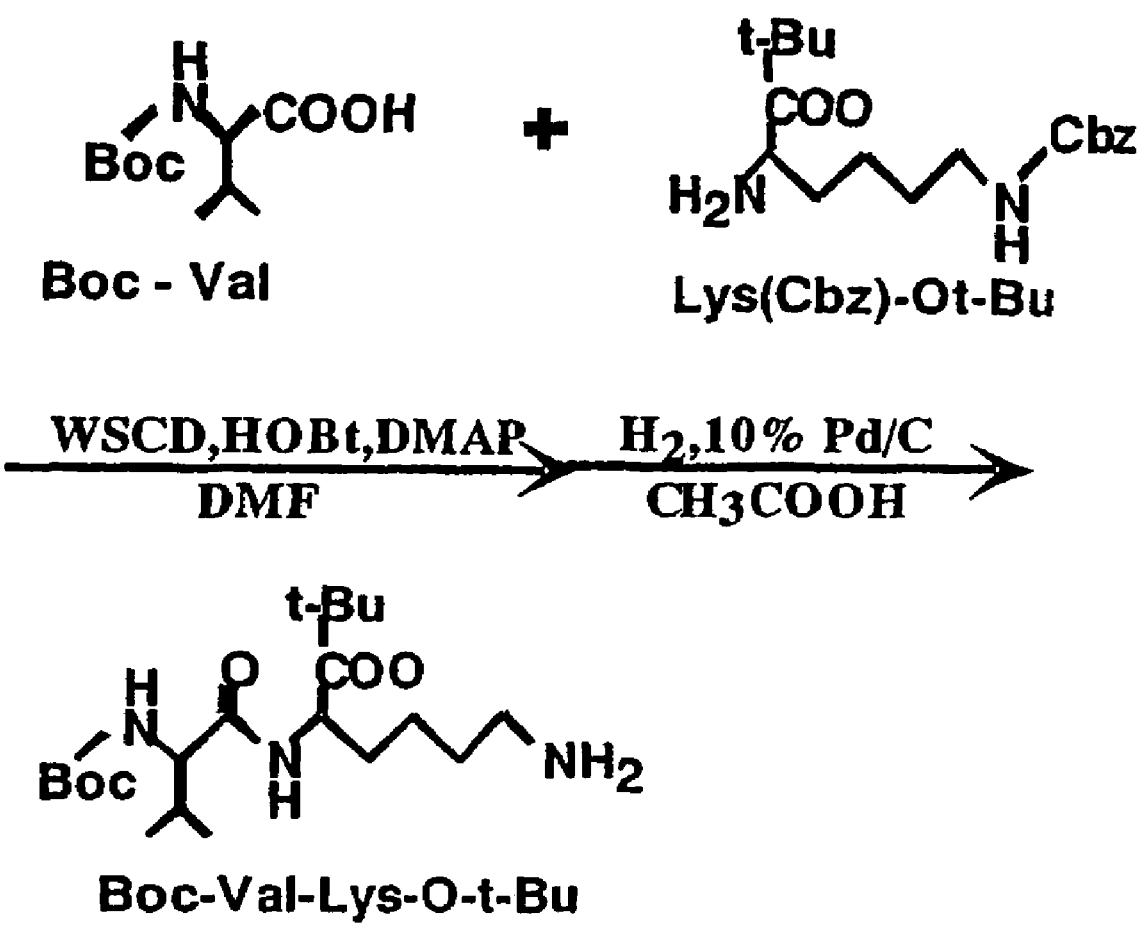
FIG. 2 is a schema showing the synthetic procedure of valyl-lysine derivative recognized by a peptide transporter.

A valyl-lysine (Val-Lys: VK) derivative, one of the dipeptide analogues recognized by a peptide transporter, was synthesized according to the method described by Abe et al. (Bioconjugate Chem. 10, 24-31, 1999) (see FIG. 2).

2-1 (Synthesis of Boc-Val-Lys(Cbz)-Ot-Bu)

Tertiary butyloxycarbonyl(Boc)-Val (2.17 g, 10 mmol), ε-benzyloxycarbonyl lysine-tert-butyl ester hydrochloride [Lys-(Cbz)-Ot-Bu-HCl (3.37 g, 10 mmol)], 1-hydroxybenzotriazole (HOBt) (4.13 g, 20 mmol), and dimethylaminopyridine (DMAP) (1.93 g, 10 mmol) were dissolved in 80 ml of N,N-dimethylformamide (DMF) respectively, and the resultant solution was stirred for 30 minutes at 0° C. Subsequently, water-soluble carbodiimide hydrochloride (WSC.HCl) (1.93 g, 10 mmol) was added and the resultant solution was stirred for about two hours at 0° C., then stirred for about four hours at room temperature, and diluted with ethyl acetate. The solution diluted with ethyl acetate was sequentially washed with 0.6 M of citric acid aqueous solution (100 ml), water (100 ml), saturated sodium bicarbonate aqueous solution (100 ml), water (100 ml), 10% of saline (100 ml). As the result, the obtained oil layer was dried with sodium sulfate and concentrated under reduced pressure, then purified by column chromatography (SiO$_2$, chloroform:methanol=75:1). Elution peak was determined by thin-layer chromatography, and the first obtained fraction was concentrated and dried under reduced pressure, and Boc-Val-Lys(Cbz)-Ot-Bu in the form of noncrystalline white powder was obtained (3.6 g, yield: 66%).

2-2 (Synthesis of Boc-Val-Lys-Ot-Bu-HCl)

The Cbz group of Boc-Val-Lys(Cbz)-Ot-Bu obtained in Example 2-1 was deprotected by the catalytic reduction method. In the presence of H$_2$ gas, Boc-Val-Lys(Cbz)-Ot-Bu was dissolved in 150 ml of acetic acid, then palladium carbon (300 mg) was added and the resultant solution was stirred for three days. The palladium carbon was removed by filtration, the solution was concentrated under reduced pressure, and the concentrated solution was subjected to ion exchange chromatography. Diaion WA-30 (HCl form) was used as an ion exchanger, and methanol-water (10:1) was used as a solvent for development. After the solution was concentrated under reduced pressure, azeotropic procedure was conducted with toluene, then white solid of Boc-Val-Lys-Ot-Bu-HCl (2.2 g, yield: 51%) was obtained.

Example 3

Figure 3:
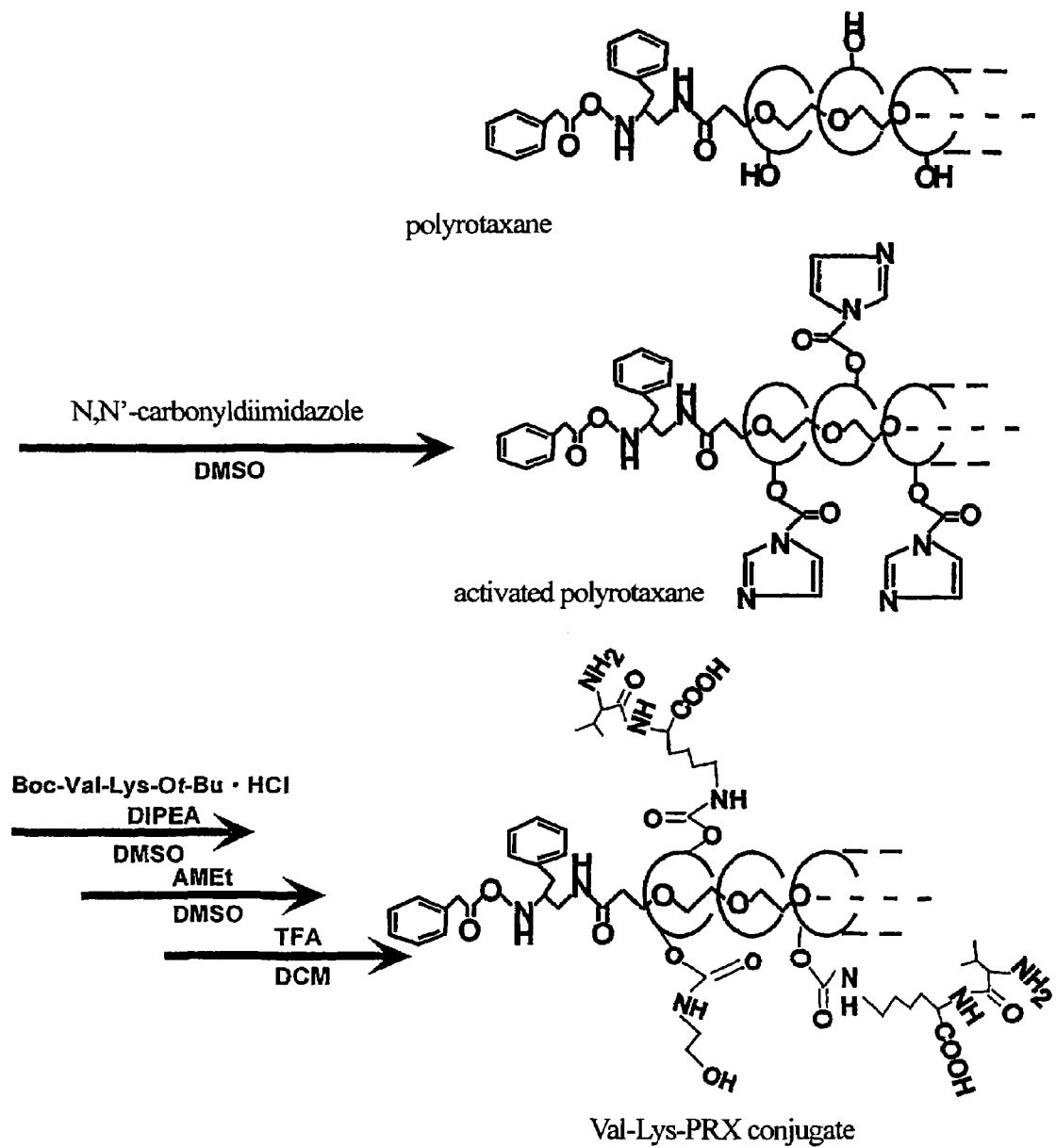
FIG. 3 is a schema showing the synthetic procedure of Val-Lys-polyrotaxane conjugate which is the tissue-specific transporter inhibitor of the present invention.

[Synthesis of Val-Lys-polyrotaxane Conjugate; See FIG. 3]

3-1 (Activation of a Hydroxyl Group in Polyrotaxane by N,N-carbonyldiimidazole)

200 mg of polyrotaxane (—OH: 3 mmol) obtained in Example 1 was dissolved in 10 ml of dimethyl sulfoxide (DMSO) under nitrogen atmosphere. After the polyrotaxane was completely dissolved, 1000 mg (6.2 mmol) of N,N-carbonyldiimidazole (CDI) was added to the solution, and the resultant solution was also stirred. Three hours later, CDI that was not reacted was removed by re-precipitation in ether, and 374 mg of CDI-activated polyrotaxane (CDI-PRX) was obtained. The activation ratio of the CDI-PRX mentioned above was 30%, when introduction into all hydroxyl groups was regarded as 100%.

3-2 (Introduction of Val-Lys into Polyrotaxane)

200 mg of the CDI-PRX mentioned above (—OH: 1.8 mmol) was dissolved in 2 ml of DMSO under nitrogen atmosphere, and 1300 mg (3.3 mmol) of Boc-Val-Lys-Ot-Bu.HCl obtained in Example 2 and 700 μl (3.5 mmol) of N,N-diisopropylethylamine (DIPEA) were added and the resultant solution was stirred for 24 hours. Subsequently, a hydroxyethylcarbamoyl (HEC) group was introduced into polyrotaxane, and 2 ml (33 mmol) of aminoethanol (AMEt) was added in order to improve water solubility, and then the resultant solution was stirred for 24 hours. After stirring, dialysis was conducted in water using dialytic membrane with molecular weight cut off 1000. After the dialysis was completed, polyrotaxane (PRX) into which Boc-Val-Lys-Ot-Bu was introduced was collected by freeze-drying. In ice-cooled condition, the collected substance was dissolved in a mixed solution of 7 ml of dichloromethane (DCM) and 3 ml of trifluoroacetate (TFA), and the resultant solution was stirred for one hour to remove a Boc group and an Ot-Bu group. Then, the sample was washed by repeating re-precipitation in ether, and was dried under reduced pressure, and white solid Val-Lys-polyrotaxane conjugate (113 mg) was obtained. Other six types of Val-Lys-polyrotaxane conjugates (VK-PRX: chemical formula 1) and two types of Val-Lys-α-CD (VK-α-CD) were synthesized by using each reagent with the amount shown in Table 4 and Table 5, by a method similar to the above-mentioned method.

TABLE 4

| VK-PRX No. | OH group in CDI-PRX (mmol) | Val-Lys (mmol) | DIPEA (mmol) | AMEt (mmol) | DMSO (ml) | Synthesized amount (mg) |
|---|---|---|---|---|---|---|
| 1 | 3.17 | 3.21 | 3.5 | — | 2 | 198 |
| 2 | 3.02 | 6.31 | 7.2 | — | 2 | 195 |
| 3 | 3.20 | 0.69 | 6.9 | 33 | 2 | 93 |
| 4 | 3.29 | 6.55 | 3.5 | 33 | 2 | 95 |
| 5 | 3.29 | 6.54 | 5.0 | 33 | 2 | 80 |
| 6 | 3.07 | 6.21 | 7.5 | 33 | 2 | 37 |
| 7 | 1.76 | 3.25 | 3.5 | 33 | 2 | 113 |

TABLE 5

| VK-α-CD No. | OH group in CDI-PRX (mmol) | Val-Lys (mmol) | DIPEA (mmol) | AMEt (mmol) | DMSO (ml) | Synthesized amount (mg) |
|---|---|---|---|---|---|---|
| 1 | 5.56 | 0.62 | 2.68 | — | 5 | 297 |
| 2 | 5.56 | 0.62 | 2.68 | 5.6 | 5 | 338 |

(Chemical Formula 1)

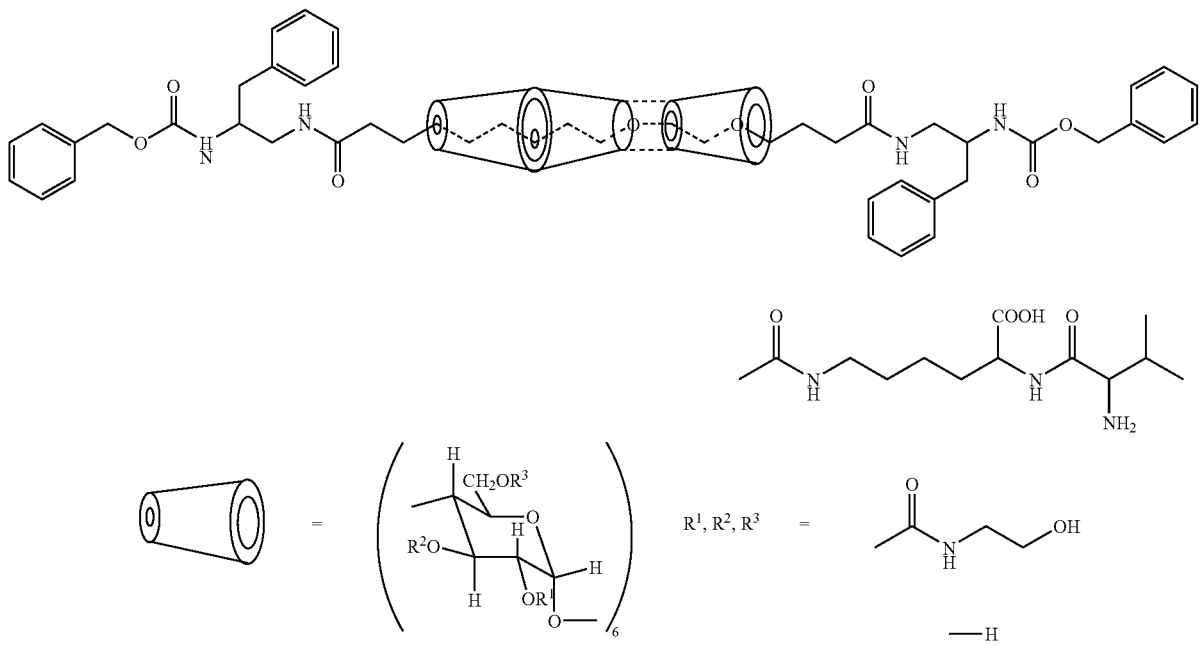

Example 4

[Characterization of Val-Lys-polyrotaxane Conjugate]

4-1 (Calculation of the number of penetrated α-CDs and introduced hydroxyehylcarbamoyl groups in Val-Lys-polyrotaxane conjugates)

The number of penetrated α-CDs in the seven types of VK-PRX mentioned above (α-CD/PRX) was calculated from the integral values of $^1$HNMR spectrum. The results are shown in Table 6.

TABLE 6

| VK-PRX No. | $M_w$ | α-CD/PRX | Val-Lys/PRX | AMEt/PRX |
|---|---|---|---|---|
| 1 | 25,300 | 21 | 1 | |
| 2 | 19,900 | 14 | 7 | |
| 3 | 30,560 | 22 | 1 | 71 |
| 4 | 34,600 | 25 | 2 | 86 |
| 5 | 24,100 | 16 | 2 | 57 |
| 6 | 18,240 | 9 | 11 | 36 |
| 7 | 43,200 | 21 | 46 | 98 |

4-2 (Quantitatation of the number of introduced Val-Lys in VK-PRX and VK-α-CD by amino acid analysis)

A small amount (1~2 mg) of each of the seven types of VK-PRX and the two types of VK-α-CD obtained in Example 3 were dissolved in 6N HCl, and $N_2$ substitution was conducted. Next, thermolysis was performed at 110° C. for about 22 hours. After removing HCl completely, the resultant solution was diluted with 0.02 N HCl (2~4 ml), and made to be a sample. The sample thus made was quantitated with an amino-acid analyzer (Hitachi amino-acid analyzer; L-8500A). Based on the composition of a Phe residue and a Val residue on both ends of VK-PRX or VK-α-CD obtained by the amino-acid analysis, the number of Val-Lys in one molecule of VK-PRX or VK-α-CD (Val-Lys/VK-PRX or Val-Lys/VK-α-CD) was calculated with the following two formulas (Table 6 and Table 7). The two formulas were reached as follows. In addition, with regard to AMEt/PRX in Table 6 and AMEt/α-CD in Table 7, the number of aminoethanol (AMET) molecules introduced into VK-PRX or VK-α-CD were calculated based on the ratio of the integral values of methylene peak from aminoethanol observed on the proton nuclear magnetic resonance ($^1$H-NMR) spectrum to the methine peak at an anomeric position in α-CD.

TABLE 7

| VK-α-CD No. | Mw | Val-Lys/α-CD | AMEt/α-CD |
|---|---|---|---|
| 1 | 1,220 | 1 | |
| 2 | 1,400 | 1 | 3 |

As one molecule of Val-Lys-AMEt-RX has two molecules of Phe residues, when the number of moles of Phe residues in the sample is $n_{phe}$, the number of moles of Val-Lys polyrotaxane conjugate ($n_{RX}$) present in the sample to be measured is shown by the formula (1).

(Mathematical Formula 1)

$$n_{RX} = \frac{n_{Phe}}{2} \qquad (1)$$

Further, when the number of moles of Val residues is $n_{val}$, and the number of moles of Val-Lys polyrotaxane conjugate is $n_{RX}$, the number of introduced Val-Lys in one molecule of Val-Lys polyrotaxane conjugate ($N_{Val-Lys}$) is shown by the formula (2).

(Mathematical Formula 2)

$$N_{Val-Lys} = \frac{n_{Val}}{n_{RX}} \quad (2)$$

Example 5

[Examination of Substrate Recognition Property to a Polymeric PEPT 1 Inhibitor Using HeLa-hPEPT 1 Cells]

In order to examine the recognition property of VK-PRX and its component, VK-α-CD, both obtained in Example 4, to PEPT 1, the inihibitory effect to the uptake of [$^3$H] Gly-Sar by using HeLa cells stably expressing hPEPT 1 (HeLa-hPEPT 1) was examined. HeLa-hPEPT 1 cells or HeLa-pcDNA (Mock) cells prepared by the method described previously (Int. J. Cancer. 88, 274-80, 2000) were placed in a multidish (Nunc) at $10^6$ cells/well and cultured in an incubator (Hirasawa) at 37° C. and 5% $CO_2$ for four days. As a broth, DMEM (Dulbecco's modified Eagle's medium; Gibco Laboratories) containing 10% FCS (Gibco Laboratories), 2 mM L-glutamine, and 1 mg/ml G418 was used. After culture, the broth was aspirated and each cell was washed three times with 1 ml of Hanks' balanced salt solution (HBSS; 0.952 mM $CaCl_2$, 5.36 mM KCl, 0.441 mM $KH_2PO_4$, 0.812 mM $MgSO_4$, 136.7 mM NaCl, 0.385 mM $Na_2HPO_4$, 25 mM D-glucose, 10 mM MES: pH 6.0) at 37° C., then preincubated for five minutes. Subsequently, 250 µl of HBSS containing each inhibitor with the concentration shown in FIG. 4 and Table 8, and [$^3$H(G)] Gly-Sar (476 nM) was added and an uptake reaction was initiated at 37° C. The inhibitors, VK-PRX (No. 1~6), were prepared such that the highest concentration of dissolved VK-PRX would be 500 µM or lower, and were filtrated through a filter, and then used for the uptake reaction. At the beginning of the reaction, the reaction solution was taken from each dish and placed into 10 µl mini vial. Then, 4 ml of liquid scintillation cocktail (Clear-sol I, Nacalai tesque) was added to the solution, and radioactivity in the reaction solution was measured by a liquid scintillation counter (LSC-5100, Aloka Co. Ltd.). Two minutes after the beginning of the reaction, the reaction solution in each dish was removed by aspiration, and the reaction was stopped by washing the cells three times with 1 ml of ice-cooled HBSS (HEPES: pH 7.4). Subsequently, 250 µl of 5 N NaOH was added to each dish to solubilize the cells (for two hours or longer), and 250 µl of 5 N HCl was added for neutralization, then the whole amount was poured into mini vial, and 4 ml of liquid scintillation cocktail (Clear-sol I, Nacalai tesque) was added, and radioactivity taken in the cells was measured.

Figure 4:
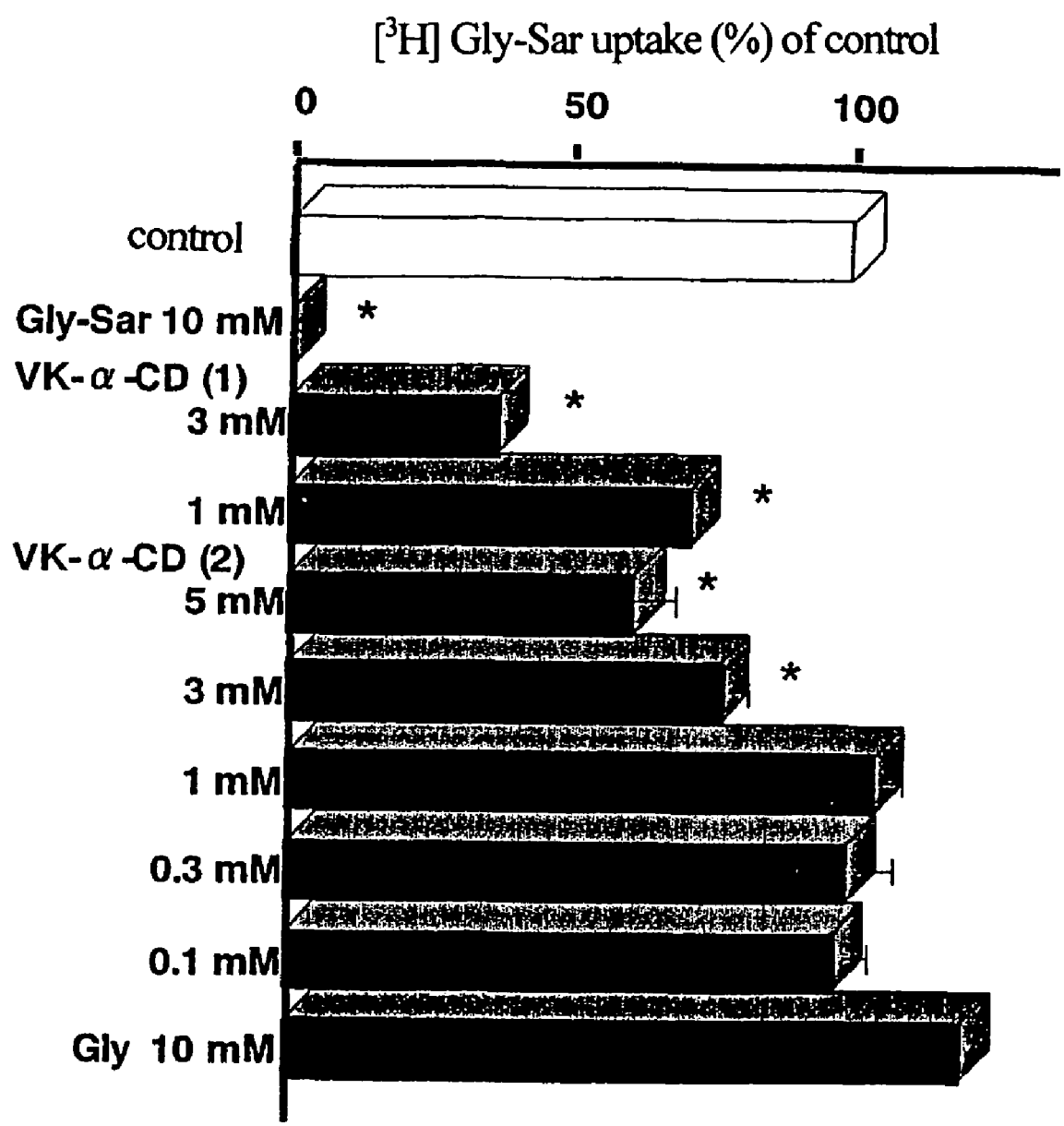
FIG. 4 is a graph showing the inhibitory effect of Val-Lys-polyrotaxanes on [$^3$H] Gly-Sar uptake by HeLa-hPEPT 1 cells.

Further, in order to measure the amount of cellular proteins after the culture mentioned above, the cultured cells were solubilized, Bio-Rad Protein Assay reagent (Bio-Rad Co.) was added, and the absorbance at 595 nm was measured. As a standard, BSA (bovine serum albumin) was used. Based on the results, the uptake amount of [$^3$H] Gly-Sar into the cells [cell/medium ratio (µl/mg·protein)] was calculated according to the formula (3). The results are shown in FIG. 4 and Table 8. The value of the control in FIG. 4 is the result of the uptake reaction conducted in the absence of the inhibitor. These results have indicated that VK-PRXs (No. 1, 2, 4, 6) reduce the uptake of [$^3$H] Gly-Sar significantly. It has been shown that the uptake of [$^3$H] Gly-Sar is also inhibited concentration-dependently in the case where VK-PRX (No. 7) and VK-α-CD are used. However, as to α-CD to which Val-Lys was not bound, significant inhibitory effect was not observed.

(Mathematical Formula 3)

$$\text{cell/medium ratio (µL/mg protein)} = \frac{\substack{\text{radioactivity taken in} \\ \text{the cells (dpm/well)}}}{\substack{\text{radioactivity concentration} \\ \text{in chemicals (dpm/mL)} \times \\ \text{the amount of proteins} \\ \text{(mg protein/well)}}} \quad (3)$$

TABLE 8

| Inhibitor | Concentration (mM) | [$^3$H] Gly-Sar uptake % of control |
|---|---|---|
| Gly-Sar | 10 | 12.93 ± 2.45 |
| Val-Lys | 3 | 21.13 ± 1.80 |
| VK-α-CD (No. 1) | 3 | 37.05 ± 1.52 |
| VK-α-CD (No. 2) | 3 | 77.09 ± 5.67 |
| α-CD | 3 | 125.87 ± 23.34 |
| VK-PRX (No. 1) | <0.5 | 37.95 ± 1.82 |
| VK-PRX (No. 2) | <0.5 | 76.68 ± 4.62 |
| VK-PRX (No. 3) | <0.5 | 131.12 ± 3.75 |
| VK-PRX (No. 4) | <0.5 | 67.32 ± 8.57 |
| VK-PRX (No. 5) | <0.5 | 94.04 ± 4.21 |
| VK-PRX (No. 6) | <0.5 | 77.20 ± 3.12 |
| VK-PRX (No. 7) | 1 | 52.93 ± 3.69 |
| VK-PRX (No. 7) | 0.5 | 76.08 ± 5.82 |
| VK-PRX (No. 7) | 0.3 | 83.95 ± 10.78 |
| VK-PRX (No. 7) | 0.1 | 104.43 ± 8.70 |
| Cefadroxil | 10 | 27.69 ± 1.44 |
| Cephalexin | 10 | 70.12 ± 1.45 |
| Gly | 10 | 97.71 ± 7.10 |

Example 6

[The Effect of Preincubation of a Polymeric PEPT 1 Inhibitor]

Figure 5:
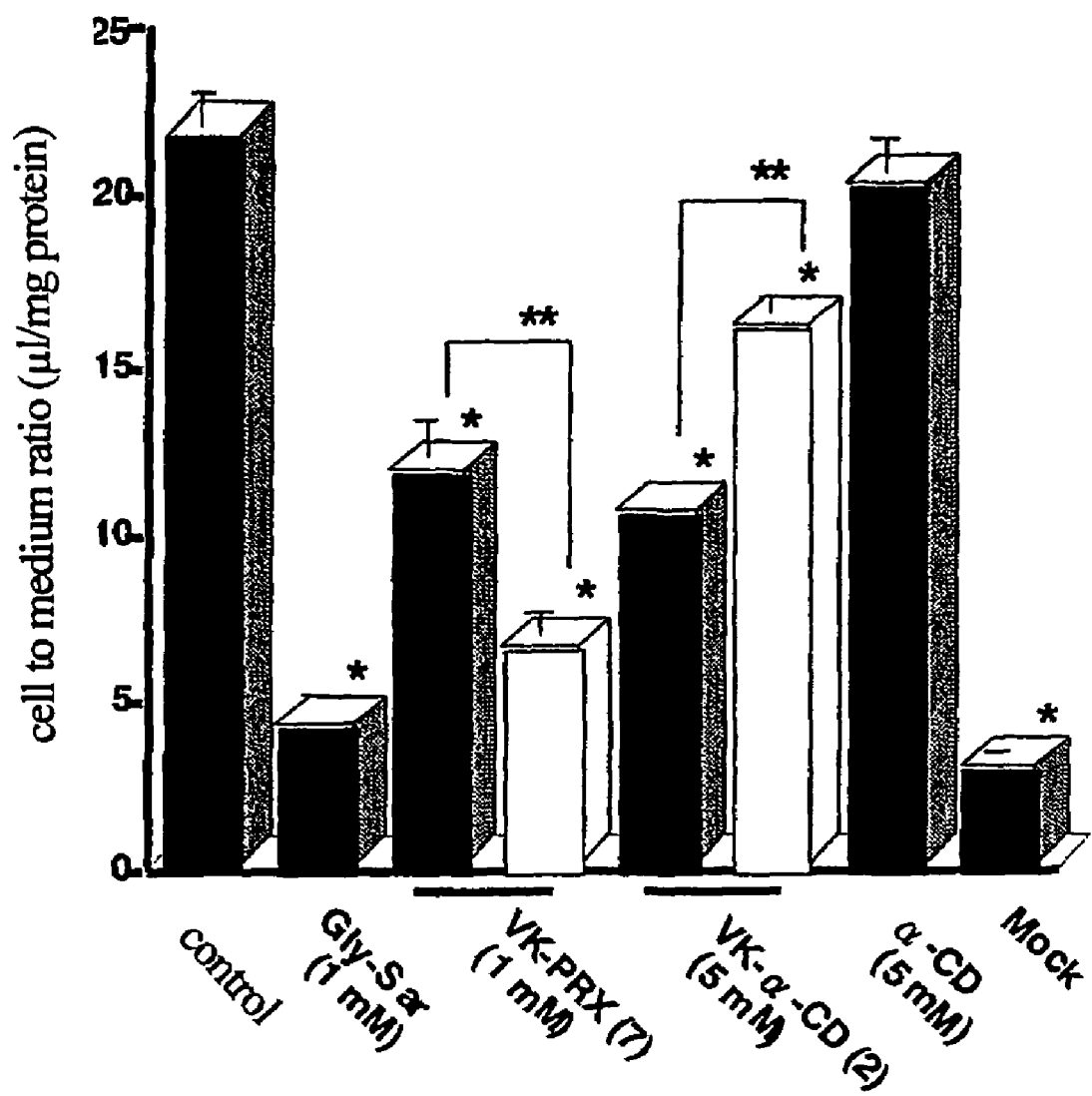
FIG. 5 is a graph showing the effect of preadministration of Val-Lys-polyrotaxanes or Val-Lys-α-cyclodextrins on [$^3$H] Gly-Sar uptake by HeLa-hPEPT 1 cells.

In order to examine the change of recognition property to PEPT 1 in polyrotaxanation of VK-α-CD, the influence of preincubation of the cells with VK-PRX (No. 7) and VK-α-CD (No. 2) on [$^3$H] Gly-Sar uptake was examined by using HeLa cells stably expressing hPEPT 1 (HeLa-hPEPT 1). In the presence or absence of each inhibitor with concentrations shown in FIG. 5, preincubation was conducted for 30 minutes (open columns), and after the reaction solution was removed, the inhibitory effect on [$^3$H] Gly-Sar uptake was measured in a manner similar to that of Example 5 except that the uptake reaction was conducted in HBSS containing the same concentration of the inhibitor and [$^3$H] Gly-Sar (476 nM) (closed columns). The results are shown in FIG. 5. In the figure, "Mock" indicates the uptake by HeLa-pcDNA 3 cells. Thus, the preincubation with VK-PRX (No. 7) or VK-α-CD (No. 2) affected the uptake of [$^3$H] Gly-Sar. With regard to VK-PRX (No. 7), significant decrease in the uptake was observed while significant increase in the uptake was observed with regard to VK-α-CD (No. 2). In addition, VK-PRX (No. 7), which is a supramolecular form of VK-α-CD (No. 2), showed stronger inhibitory effect, however, no inhibitory effect of α-CD to which Val-Lys was not bound was observed.

Example 7

[Evaluation of Absorption Inhibitory Effect of VK-PRX by Changes in Pharmacokinetics of Cefadroxil (CDX)]

Recently, it is reported that T-1095, a glucose transporter inhibitor in the kidney, ameliorates hyperglycemic conditions in STZ rats (Streptozotocin-induced diabetic rats)(Metabolism, 49, 990-5, 2000). This report suggests that clinical conditions could be ameliorated by suppressing the transporter function and controlling the transportation of bioactive substances, and there is an expectation as a drug target. Further, it has been reported that bioavailability of cefadroxil [CDX: (chemical formula 2)], a β-lactam antibiotic which is a substrate of PEPT 1 in human, is decreased by the co administration of cephalexin [CEX: (chemical formula 3)] which is a β-lactam antibiotic (Eur. J. Clin. Pharmacol. 41, 179-83, 1991). This report indicates that absorption of CDX through the digestive tract via PEPT 1 was suppressed by CEX, which is also a substrate of PEPT 1. Therefore, the inhibitory effect of a PEPT 1 inhibitor on CDX absorption was examined by using rats.

(Chemical Formula 2)

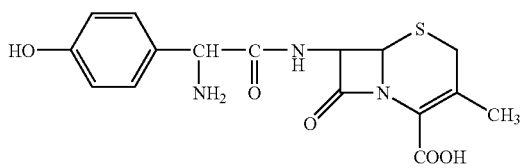

(Chemical Formula 3)

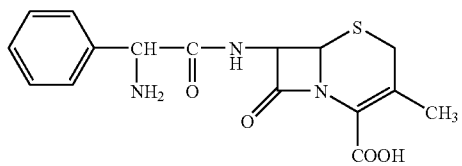

SD (Sprague-Dawley) rats (male; Japan SLC, Inc.) of 7~8 weeks of age were anesthetized by intraperitoneal administration of 50 mg/kg of Nembutal (Dainabbot, Inc.), and after fixing their backs, jugular veins and femoral veins (only when instant intravenous injection was performed) were cannulated [silicon tube, inner diameter×outer diameter (0.5×1)], and the tip end of the cannula was inserted subcutaneously and passed through from the back of the neck, then the cut was stitched up. Subsequently, the animals were starved overnight (about 18 hours) and each pharmaceutical was administered orally via oral sonde, or administered via femoral vein. After administering each pharmaceutical, 400 μl of the blood was collected from the cannulation tube over time, and CDX concentration in the plasma was measured by the method mentioned below, then each parameter was calculated by the formula (4) or the formula (5), the formula (6), the formula (7), and the formula (8), and analyzed according to the compartment model analysis of WinNonlin (Scientific Consulting Inc.) (Edited by Akira Tsuji, "Comprehensible Biopharmaceutics", Hirokawa Shoten, 178-188, 1996).

400 μl of the collected blood mentioned above was substituted with the same amount of saline, and the blood was dispensed into 1.5 ml microtube, and centrifuged (12000 rpm, 5 minutes, 4° C.) to extract the plasma. 150 μl of the plasma was transferred to 1.5 ml microtube, and added with the same amount of acetonitrile for deprotein treatment. After centrifugation (12000 rpm, 5 minutes, 4° C.), 250 μl of supernatant was transferred to 1.5 ml microtube, and evaporated to dryness, then reconstructed according to the HPLC condition mentioned below. As a column, TSKgel ODS-80Ts (Toyo Soda) was used, and as a pump, an ultraviolet-visible light detector, an intelligent autosampler, and a column oven, 880-PU, 875-UV, AS-1555-10, and Co-1565 (all from JASCO Corporation) were used respectively, and as an integrator, Chromatopac C-R3A (Shimadzu Corporation) was used. At the column temperature 35° C., 7% of acetonitrile (containing 0.1 M of acetic acid buffer (pH 3.0) and 0.01 M of 1-pentasulfonic acid sodium) was used as a mobile phase for separating elution at flow rate 0.9 ml/min. The detection was conducted at wavelength 240 nm, and CDX concentration in the plasma was determined.

(Mathematical Formula 4)

$$C = \frac{ka \cdot F \cdot D\{\exp(-ke \cdot t) - \exp(-ka \cdot t)\}}{Vd(ka - ke)} \quad (4)$$

In the formula, C, F, D, ka, ke, Vd and t represent CDX concentration in the plasma, absorptance, dosage, absorption rate constant, elimination rate constant, distribution volume, and time interval between the drug administration and blood collection, respectively.

(Mathematical Formula 5)

$$C = A \cdot \exp(-\alpha \cdot t) + B \cdot \exp(-\beta \cdot t) \quad (5)$$

With the proviso that $A = D(k_{21} - \alpha)/V_1(\beta - \alpha)$
$B = D(k_{21} - \beta)/V_1(\alpha - \beta)$ In the formula, α, β and $V_1$ represent gradient of distribution phase, gradient of elimination phase, and distribution volume of central compartment, respectively.

(Mathematical Formula 6)

$$AUC_{0-\infty} = AUC_{0-6} + C_6/ke \quad (6)$$

In the formula, AUC represents area under the plasma concentration-time curve, $C_6$ represents concentration of a drug in the plasma 6 hours after the administration, respectively.

(Mathematical Formula 7)

$$CL = Dose/AUC_{0-\infty} \quad (7)$$

In the formula, CL represents total clearance, Dose represents the dose of the drug, respectively.

(Mathematical Formula 8)

$$Vd = CL/ke \quad (8)$$

7-1 (The Inhibitory Effect of CEX on CDX Transportation Via PEPT 1 Using Rats)

Figure 6:
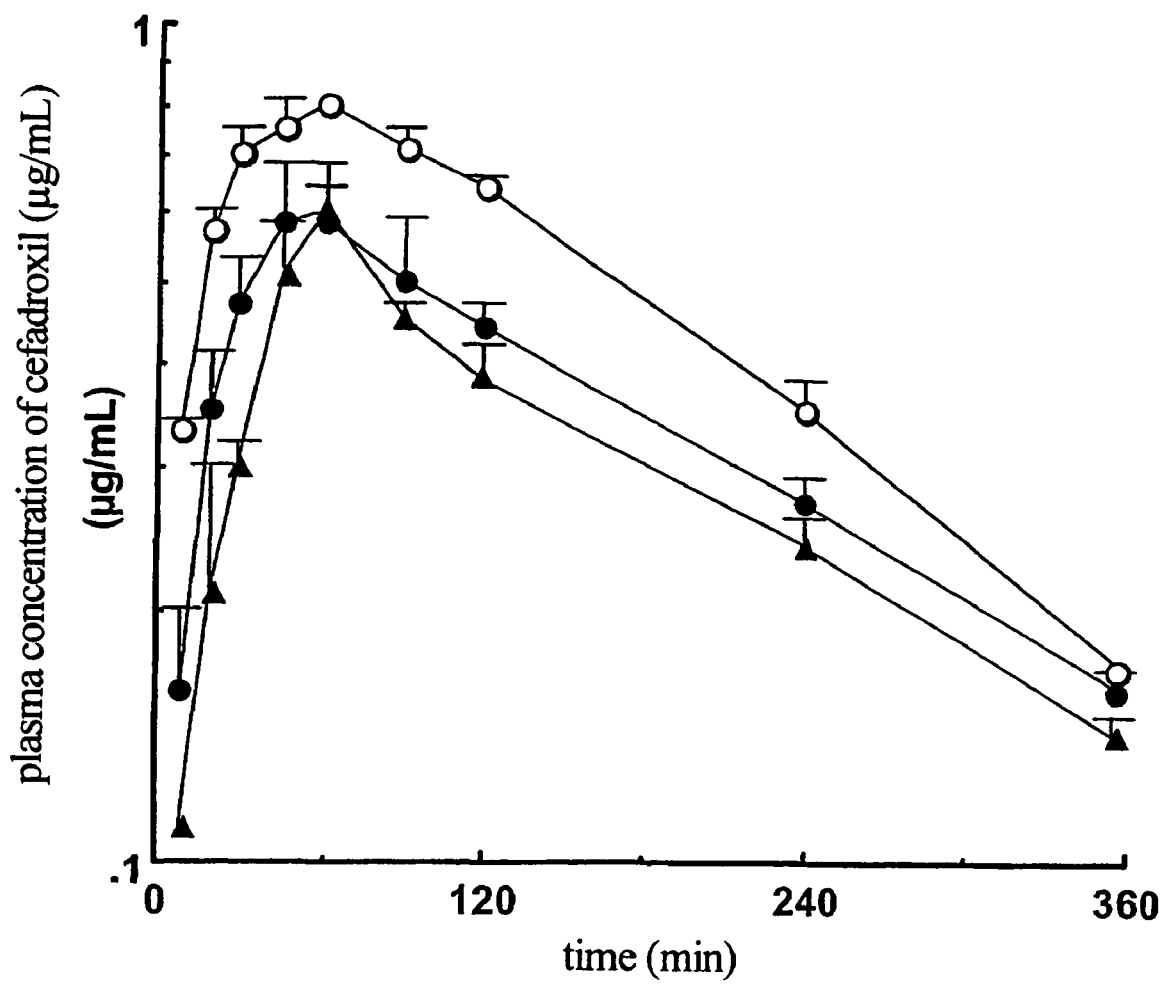
FIG. 6 is a graph showing the result of time course change of cefadroxil concentration in the plasma after administration with or without cephalexin to rats.

It has been reported that bioavailability of CDX, which is a substrate of PEPT 1, is decreased by the co administration of CEX, which is a β-lactam antibiotic in human (Eur. J. Clin. Pharmacol., 41, 179-83, 1991). In order to elucidate the inhibitory effect of VK-PRX on PEPT 1, 2.5 mg/kg CDX (○), 5 mg/kg CDX (●), or 2.5 mg/kg CDX and 45 mg/kg CEX (▼) as pharmaceuticals were orally administered to the rats mentioned above, and it was examined whether CEX inhibited the absorption of CDX in rats by the method described in Example 7. With regard to 2.5 mg/kg CDX and 45 mg/kg CEX (▼), CEX was orally administered to the rats 30 minutes before the administration of CDX. Each pharmacokinetic parameter of the above-mentioned rats was calculated based on the change in the CDX concentration in the blood, with the formula (4), the formula (6), the formula (7), and the formula (8), and evaluated. The results are shown in FIG. 6 and Table 9. Values shown in the figure and the table are the mean±S.E.M. of three to four independent experiments. The results of oral administration of CDX at 2.5 mg/kg or 5 mg/kg have shown saturation phenomenon in $AUC_{0-\infty}$ and Cmax. In addition, when CDX was administered at 2.5 mg/kg, the sufficient absorptance, 86%, was obtained. It has been shown that CDX is appropriate as a marker compound which evaluates absorption activity via PEPT 1, taking into account that CDX is stable in a living organism. Further, in the case where CDX (2.5 mg/kg) was administered after CEX (45 mg/kg) was preadministered, area under the plasma concentration-time curve ($AUC_{0-\infty}$) was decreased by about 30%, absorption rate constant (ka) and maximum plasma concentration (Cmax) were significantly decreased from 2.42 to 1.53 $hr^{-1}$ and 0.8 to 0.5 μg/ml, respectively, in comparison to the case where CDX alone was administered. The above results have reproduced the report, which deals with the cases of human, in rats.

TABLE 9

|  | Dose (mg/kg) | | |
| --- | --- | --- | --- |
|  | 2.5 | 5 | 2.5 + 45 |
| ka ($hr^{-1}$) | 2.42 ± 0.08 | 2.09 ± 0.23 | 1.53 ± 0.27* |
| ke ($hr^{-1}$) | 0.33 ± 0.02 | 0.31 ± 0.03 | 0.37 ± 0.03 |
| Tmax (hr) | 0.95 ± 0.03 | 1.09 ± 0.08 | 1.25 ± 0.13 |
| Cmax (μg/mL) | 0.80 ± 0.03 | 0.56 ± 0.07 | 0.50 ± 0.04 |
| $AUC_{0-\infty}$ (μg · min/mL) | 198 ± 4.82 | 162 ± 13.3 | 144 ± 5.21 |

7-2 (The Change in Absorption Inhibitory Effect by VK-PRX Type)

Figure 7:
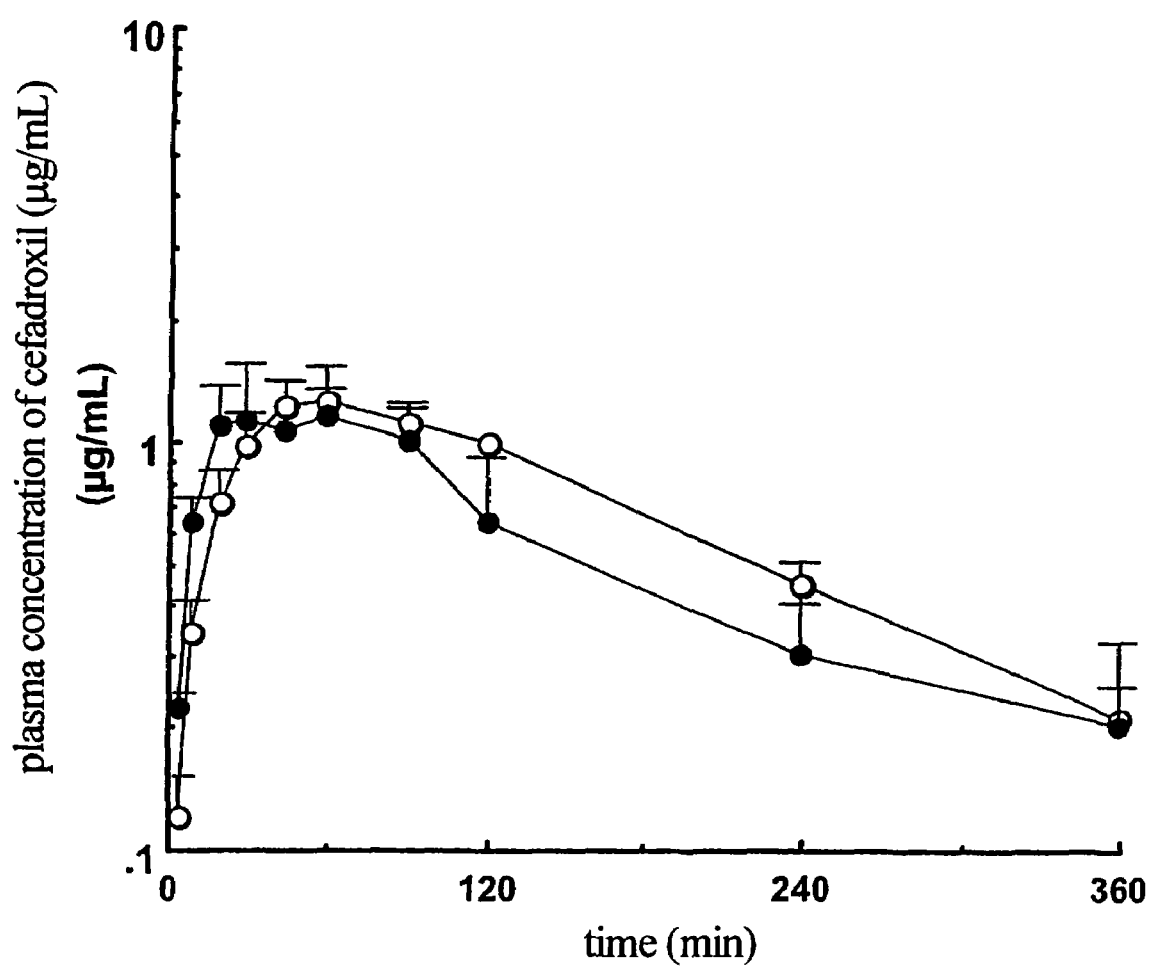
FIG. 7 is a graph showing the result of time course change of cefadroxil concentration in the plasma after administration with or without Val-Lys-polyrotaxane (No. 2) to rats.
Figure 8:
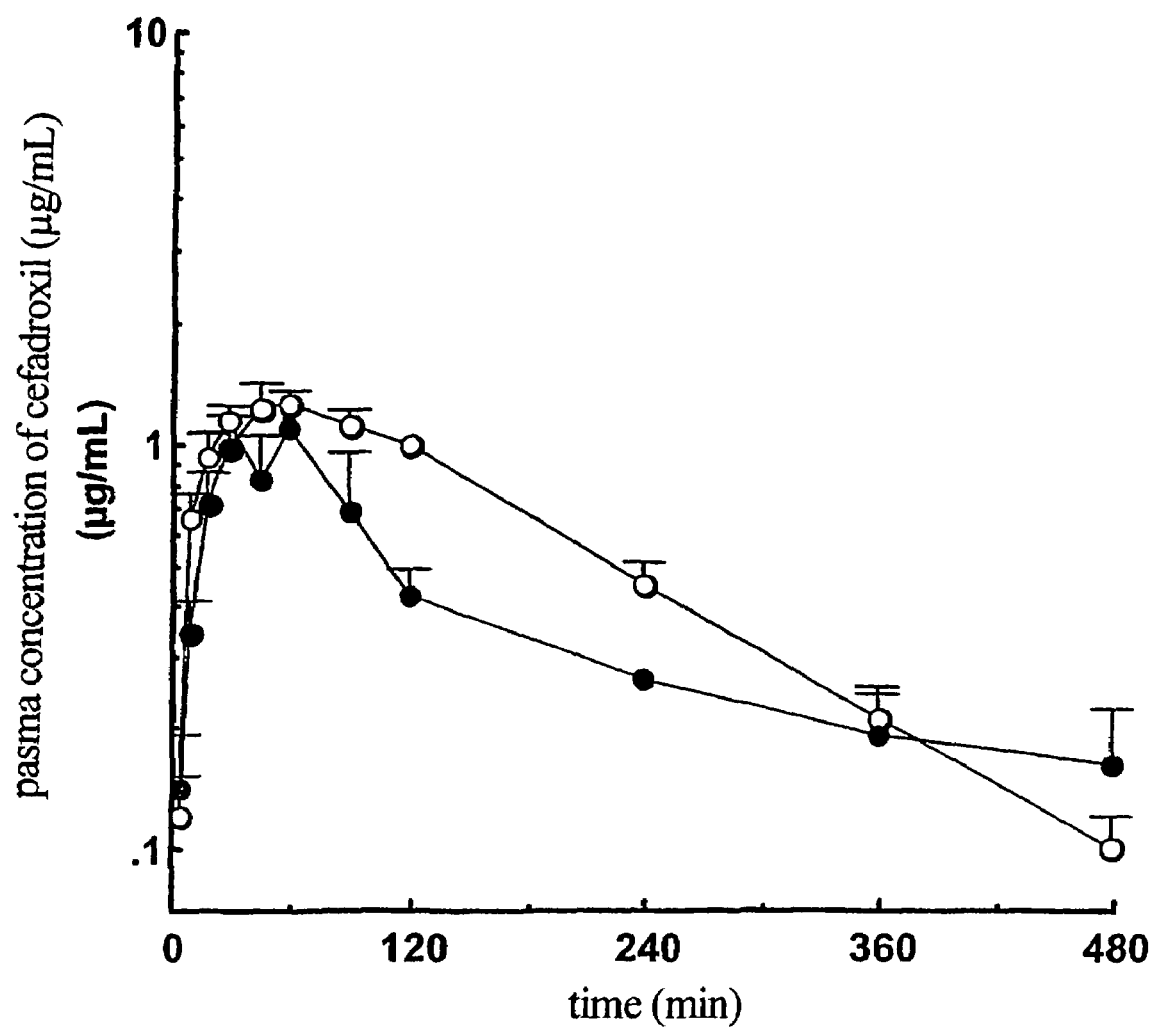
FIG. 8 is a graph showing the result of time course change of cefadroxil concentration in the plasma after administration with or without Val-Lys-polyrotaxane (No. 7) to rats.

Next, 5 mg/kg CDX alone (○), or 10 mg/kg VK-PRK [VK-PRK suspended in 0.1% of sodium polyacrylate (PANA) in saline] and 5 mg/kg CDX (●) were used as pharmaceuticals and orally administered to the rats mentioned above, and it was examined whether VK-PRX inhibited the absorption of CDX in rats by the method described in Example 7. The above-mentioned VK-PRK was administered to the rats 30 minutes before the administration of 5 mg/kg CDX (●). Then each pharmacokinetic parameter was calculated based on the change in the CDX concentration in the blood, with the formula (4), the formula (6), the formula (7), and the formula (8), and evaluated. The results obtained with VK-PRK (No. 2) are shown in FIG. 7 and Table 10, and the results obtained with VK-PRK (No. 7) are shown in FIG. 8 and Table 11. Values shown in the figures are the mean±S.E.M. of two to four independent experiments, and values shown in the tables are the mean±S.E.M. of three independent experiments. VK-PRK (No. 2) or VK-PRK (No. 7) was coadministered with CDX, but there was no significant difference observed in $AUC_{0-\infty}$ in comparison to the case where CDX alone was administered. Further, there was no significant difference observed with regard to other parameters, either. Judging from these results, it is presumed that the dose of CDX (5 mg/kg) mentioned above was a condition wherein the effect of VK-PRX (No. 2) was difficult to be detected because the absorption through the digestive tract had already been saturated.

TABLE 10

| Parameter | CDX | CDX + VK-RX (2) |
| --- | --- | --- |
| ka ($hr^{-1}$) | 1.50 ± 0.24 | 3.21 ± 0.18 |
| ke ($hr^{-1}$) | 0.54 ± 0.06 | 0.49 ± 0.10 |
| Tmax (hr) | 1.13 ± 0.11 | 0.70 ± 0.02 |
| Cmax (μg/m) | 1.22 ± 0.08 | 1.17 ± 0.28 |
| $AUC_{0-\infty}$ (μg · min/mL) | 272 ± 9.27 | 244 ± 93.4 |

TABLE 11

| Parameter | CDX | CDX + VK-RX (7) |
| --- | --- | --- |
| ka ($hr^{-1}$) | 1.50 ± 0.24 | 3.33 ± 0.00 |
| ke ($hr^{-1}$) | 0.54 ± 0.06 | 0.63 ± 0.25 |
| Tmax (hr) | 1.13 ± 0.11 | 0.64 ± 0.10 |
| Cmax (μg/mL) | 1.22 ± 0.08 | 1.04 ± 0.11 |
| $AUC_{0-\infty}$ (μg · min/mL) | 272 ± 9.27 | 220 ± 20.2 |

7-3 (The Dose of VK-PRX and its Effect)

Figure 9:
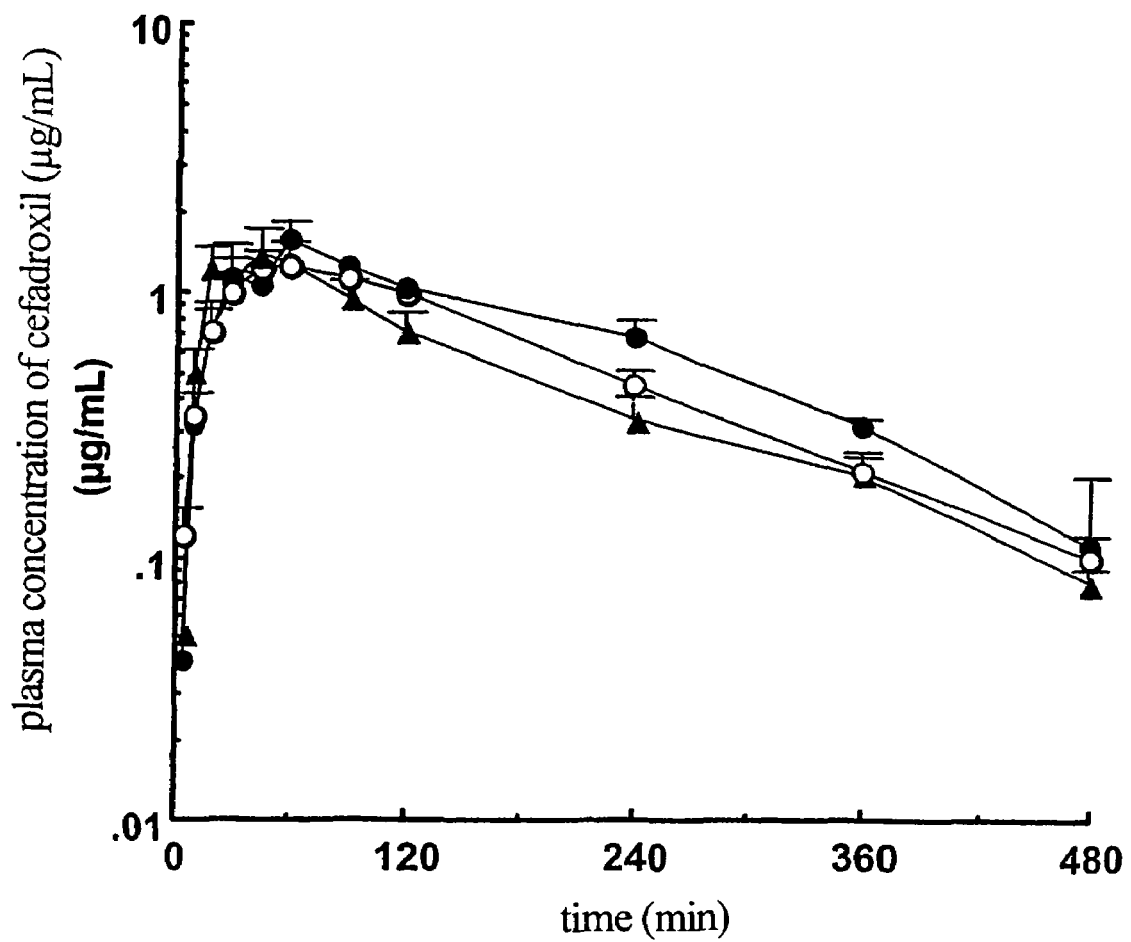
FIG. 9 is a graph showing the result of time course change of cefadroxil concentration in the plasma after administration with CDX, and cephalexin or Val-Lys-polyrotaxane (No. 2) to rats.

As in the method described in Example 7, 5 mg/kg CDX alone (○), 10 mg/kg CEX and 5 mg/kg CDX (▼), or 5.7 mg/kg VK-PRK (No. 2) and 5 mg/kg CDX (●) were orally administered to rats simultaneously, and each pharmacokinetic parameter was calculated and evaluated. The results are shown in FIG. 9 and Table 12. Values shown in the figure and the table are the mean±S.E.M. of two to four independent experiments. As in the case where 10 mg/kg VK-PRX (No. 2) was coadministered with CDX (FIG. 7 and Table 10), in the case where 5.7 mg/kg VK-PRX (No. 2) was coadministered with CDX, there was no significant difference observed in $AUC_{0-\infty}$ in comparison to the case where CDX alone was administered. Further, there was no significant difference observed with regard to other parameters, either.

TABLE 12

| Parameter | CDX | CDX + CEX | CDX + VK-PRX (2) |
| --- | --- | --- | --- |
| ka ($hr^{-1}$) | 1.50 ± 0.24 | 2.41 ± 0.49 | 1.37 ± 0.73 |
| ke ($hr^{-1}$) | 0.54 ± 0.06 | 0.68 ± 0.19 | 0.49 ± 0.13 |
| Tmax (hr) | 1.13 ± 0.11 | 0.79 ± 0.07 | 1.32 ± 0.29 |
| Cmax (μg/mL) | 1.22 ± 0.08 | 1.29 ± 0.21 | 1.32 ± 0.08 |
| $AUC_{0-\infty}$ (μg · min/mL) | 272 ± 9.27 | 247 ± 23.6 | 337 ± 29.9 |

7-4 (The Influence of a Suspending Agent on VK-PRX Effect)

Figure 10:
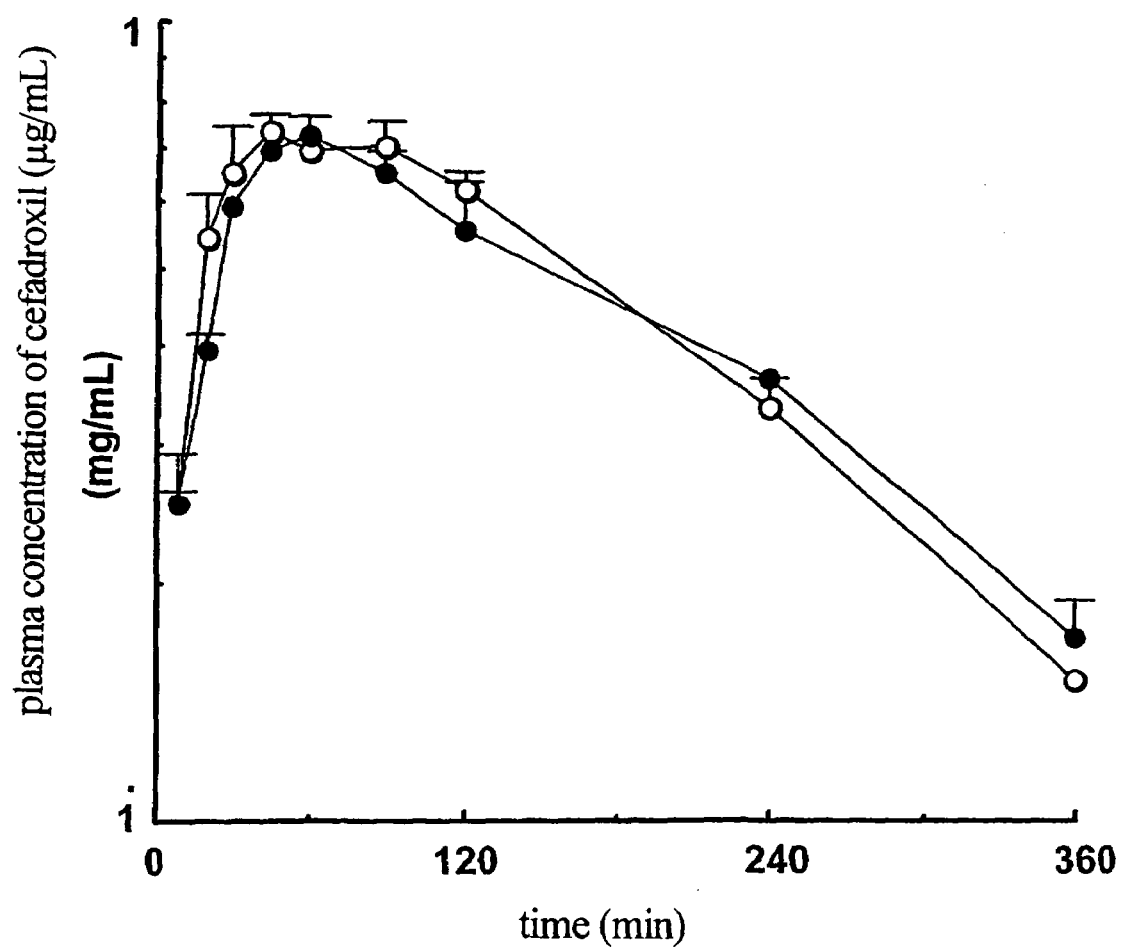
FIG. 10 is a graph showing the result of time course change of cefadroxil concentration in the plasma after administration with or without Val-Lys-polyrotaxane (No. 7) to rats.
Figure 11:
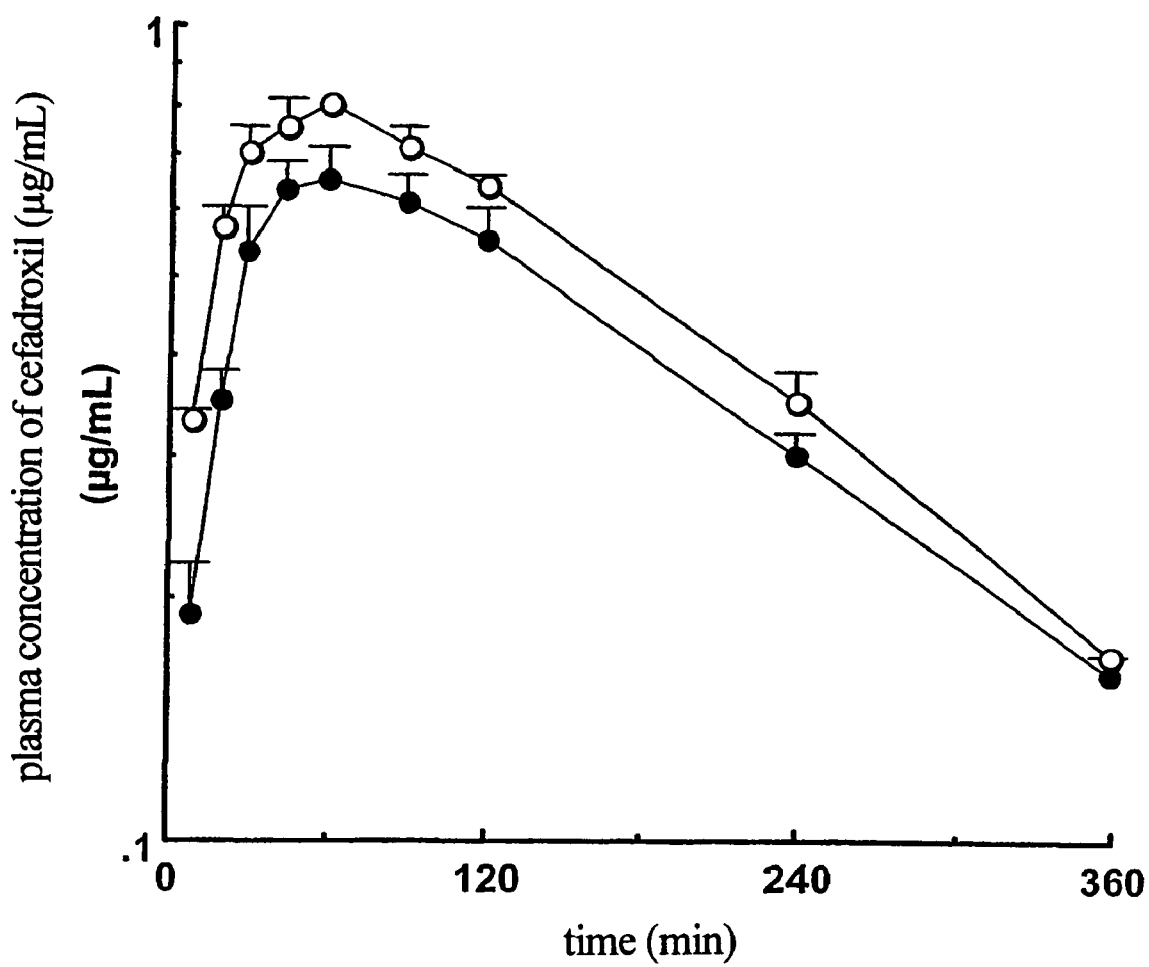
FIG. 11 is a graph showing the result of time course change of cefadroxil concentration in the plasma after administration with or without Val-Lys-polyrotaxane (No. 7) to rats.

Next, in order to examine the difference in the effect of VK-PRX between the case where each pharmaceutical was suspended in saline containing 0.1% of sodium polyacrylate (PANA) which is a suspending agent (FIG. 10), and the case where each pharmaceutical was not suspended (FIG. 11), 10 mg/kg VK-PRK (No. 7) and 2.5 mg/kg CDX (●), or 2.5 mg/kg CDX alone were orally administered, and each pharmacokinetic parameter in each rat was calculated according to the method described in Example 7 and evaluated. VK-PRK was orally administered 30 minutes before CDX administration. The results of the case where each pharmaceutical was suspended in PANA are shown in FIG. 10 and Table 13, and the results of the case where each pharmaceutical was not suspended in PANA are shown in FIG. 11 and Table 14. Values shown in FIG. 10, FIG. 11 and Table 14 are the mean±S.E.M. of four independent experiments, and values shown in Table 13 are the mean±S.E.M. of three independent experiments. These results have indicated that in the case where VK-PRK (No. 7) was suspended in a suspending agent and coadministered with CDX, there was no significant difference observed in $AUC_{0-\infty}$ in comparison to the case where CDX alone was administered, and that there was no significant difference observed with regard to other parameters, either. On the other hand, it has been found that $AUC_{0-\infty}$ significantly decreases when VK-PRK is administered under the same condition excluding the suspension in PANA. Further, by co administration of VK-PRK, ka and Cmax were significantly decreased from 2.42 to 1.75 $hr^{-1}$ and 0.8 to 0.64

µg/ml, respectively, and Tmax was significantly prolonged from 0.95 to 1.18 hr. However, no significant difference was observed in the elimination rate constant (ke).

TABLE 13

| Parameter | CDX | CDX + VK-RX (7) |
|---|---|---|
| ka (hr$^{-1}$) | 2.12 ± 0.45 | 1.88 ± 0.03 |
| ke (hr$^{-1}$) | 0.37 ± 0.02 | 0.33 ± 0.02 |
| Tmax (hr) | 1.04 ± 0.12 | 1.13 ± 0.04 |
| Cmax (µg/mL) | 0.76 ± 0.04 | 0.69 ± 0.02 |
| AUC$_{0-\infty}$ (µg · min/mL) | 186 ± 9.15 | 188 ± 7.42 |

TABLE 14

| Parameter | CDX | CDX + VK-RX (7) |
|---|---|---|
| ka (hr$^{-1}$) | 2.42 ± 0.08 | 1.75 ± 0.19 |
| ke (hr$^{-1}$) | 0.33 ± 0.02 | 0.34 ± 0.03 |
| Tmax (hr) | 0.95 ± 0.03 | 1.18 ± 0.05 |
| Cmax (µg/mL) | 0.80 ± 0.03 | 0.64 ± 0.05 |
| AUC$_{0-\infty}$ (µg · min/mL) | 198 ± 4.82 | 175 ± 6.26 |

7-5 (The Effectiveness of Preadministration of VK-PRX)

Figure 12:
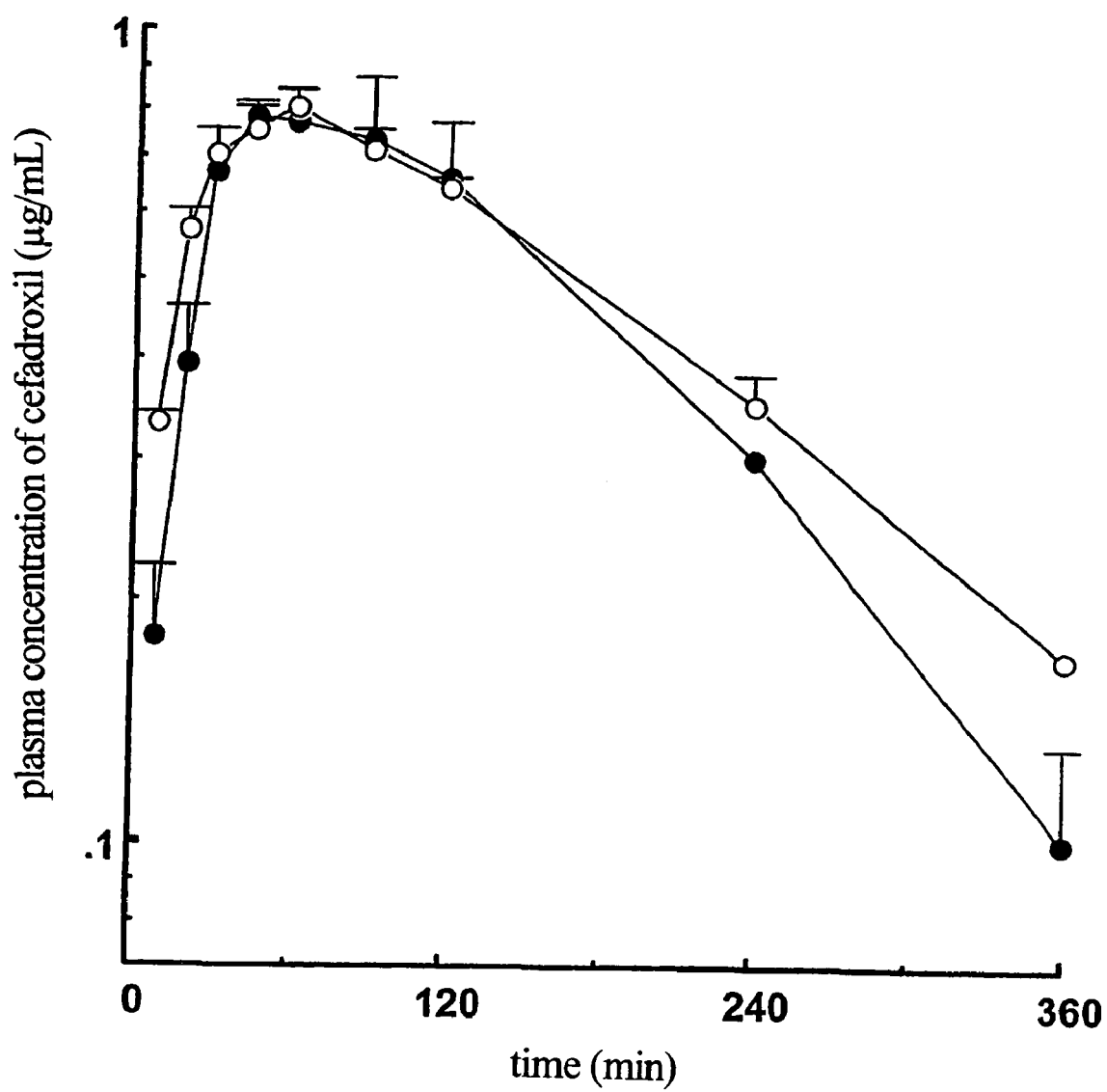
FIG. 12 is a graph showing the result of time course change of cefadroxil concentration in the plasma after administration with or without Val-Lys-polyrotaxane (No. 7) to rats.

The effectiveness of preadministration of VK-PRX was also examined. Each pharmacokinetic parameter, in the case where 2.5 mg/kg CDX and 10 mg/kg VK-PRX (No. 7) were orally coadministered (●), or 2.5 mg/kg CDX alone were orally administered (○), was calculated in the same manner as the method described in Example 7 and evaluated. The results are shown in FIG. 12 and Table 15. Values shown in the figure are the mean±S.E.M. of three independent experiments, and values shown in the table are the mean±S.E.M. of four independent experiments. As the results, in the case where VK-PRX (No. 7) was coadministered with CDX, there was no significant difference observed in AUC$_{0-\infty}$ in comparison to the case where CDX alone was administered. However, in the case where VK-PRX (No. 7) was preadministered and CDX was administered 30 minutes later (FIG. 11 and Table 14), significant decrease of AUC$_{0-\infty}$ was observed, and significant decrease of ka was observed regardless of whether preadministration was conducted or not.

TABLE 15

| Parameter | CDX | CDX + VK-RX (7) |
|---|---|---|
| ka (hr$^{-1}$) | 2.42 ± 0.08 | 1.29 ± 0.28 |
| ke (hr$^{-1}$) | 0.33 ± 0.02 | 0.57 ± 0.13 |
| Tmax (h) | 0.95 ± 0.03 | 1.18 ± 0.08 |
| Cmax (µg/mL) | 0.80 ± 0.03 | 0.78 ± 0.08 |
| AUC$_{0-\infty}$ (µg · min/mL) | 198 ± 4.82 | 175 ± 9.98 |

Example 8

[The Influence after VK-PRX Intravenous Injection on Pharmacokinetics of CDX]

Figure 13:
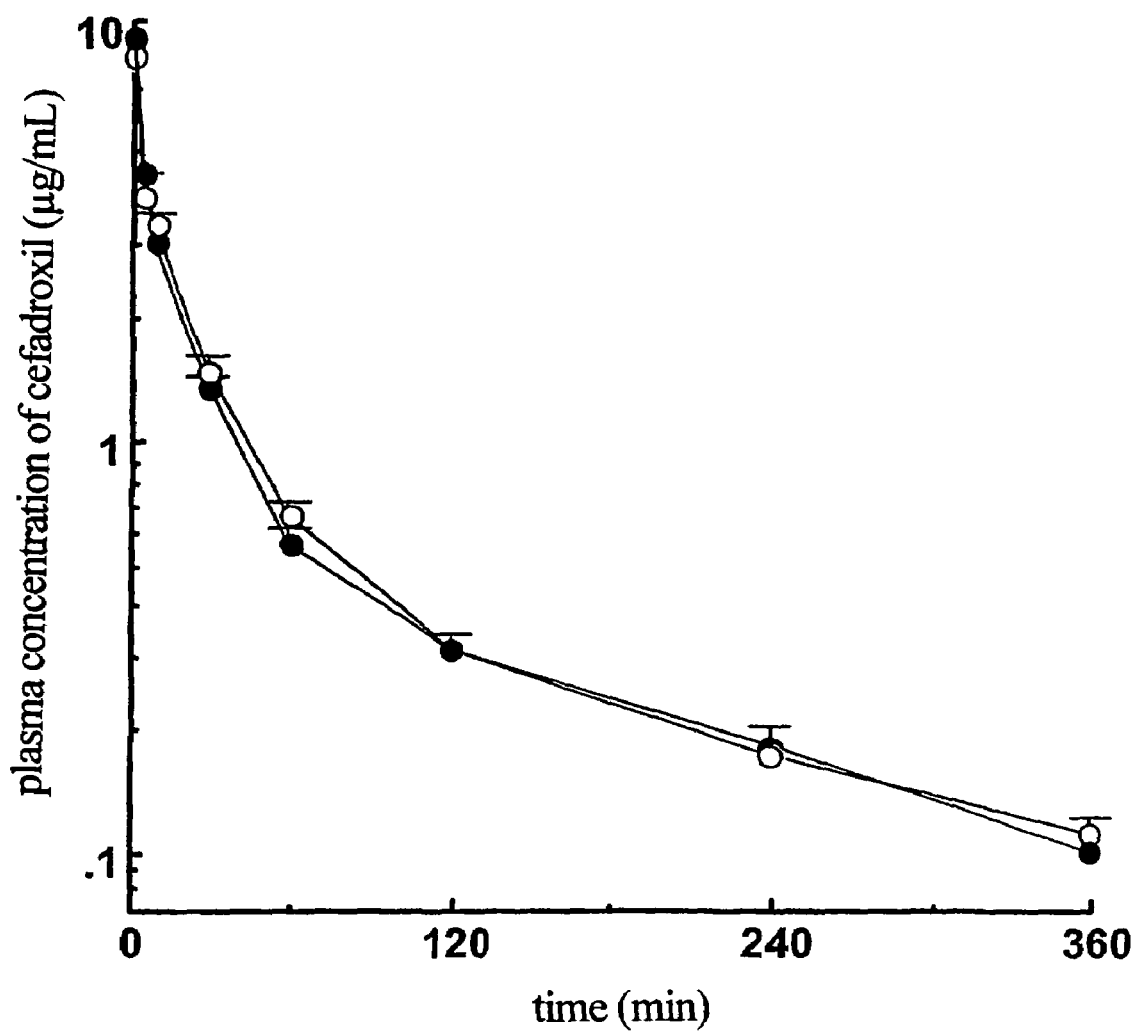
FIG. 13 is a graph showing the result of time course change of cefadroxil concentration in the plasma after instant intravenous injection of CDX and simultaneous oral administration with Val-Lys-polyrotaxane (No. 7) to rats.

Since VK-PRX is a polymer compound, it is not presumed to be absorbed through the digestive tract. However, it is also known that orally administered CEX prompts the excretion of CDX, and therefore, it is not necessarily explicable if the effect of VK-PRX that decreases AUC$_{0-\infty}$ of CDX means the decrease of absorbency only. On the other hand, CDX is known to show nonlinearity in the reabsorption through the kidney (Drug Metab. Dispos. 21, 215-7, 1993, Drug Metab. Dispos. 22, 447-50, 1994). In addition, oligopeptide transporters are involved in the reabsorption. Therefore, in order to compare the influence on CDX clearance (CL: renal excretion) in rats instantly and intravenously injected with 2.5 mg/kg CDX, and simultaneously administered with 10 mg/kg VK-PRX (No. 7) [VK-PRK dissolved in saline] orally (○), to that in rats instantly and intravenously injected with 2.5 mg/kg CDX (●), each pharmacokinetic parameter was calculated according to the method described in Example 7 and evaluated (FIG. 13 and Table 16). Values shown in the figure and the table are the mean±S.E.M. of three independent experiments. As the results, the administration of VK-PRX did not affect the change in the CDX concentration in the plasma, indicating that the change of AUC$_{0-\infty}$ mentioned above was caused not by the influence on renal excretion/reabsorption process, but by absorption through the digestive tract. Further, it has been already revealed that physical stability of a peptide carried by PRX increases (Pharm. Res. 16, 1331-1343, 1999), and the obtained results support that VK-PRX is a compound which is not absorbed or is hard to be absorbed through the digestive tract. These results have revealed that a polymeric PEPT 1 inhibitor as a nonabsorbent compound inhibits the PEPT 1-mediated absorption. This result leads to the suppression of PEPT 1-mediated protein absorption.

TABLE 16

| Parameter | CDX | CDX + VK-RX (7) |
|---|---|---|
| AUC$_{0-\infty}$ (µg · min/mL) | 229 ± 8.41 | 222 ± 5.09 |
| Vdss (mL) | 162 ± 8.99 | 134 ± 10.3 |
| CLtot (mL/min) | 11.0 ± 0.41 | 11.3 ± 0.26 |
| ke (hr$^{-1}$) | 4.10 ± 0.28 | 5.12 ± 0.46 |

INDUSTRIAL APPLICABILITY

As the tissue-specific transporter inhibitor of the present invention is not absorbed or is hard to be absorbed through the small intestine, it can prevent deterioration in the QOL, which is caused by diet therapy, of patients who suffer from tissue dysfunction diseases or renal failure by specifically decreasing the absorption of nutrients through the small intestine. In addition, the tissue-specific transporter inhibitor is useful for preventive medicine that prevents the onset of tissue diseases such as renal diseases and conservative treatments that prevent the progress of renal failure into dialysis.

The invention will now be further described by the following numbered paragraphs:

1. A tissue-specific transporter function inhibitor which has both a ligand structure recognized by a tissue-specific transporter and a polymeric molecular structure incapable of passing through a membrane tissue.
2. The tissue-specific transporter function inhibitor according to paragraph 1, wherein the polymeric molecular structure incapable of passing through a membrane tissue is a supramolecular structure.
3. The tissue-specific transporter function inhibitor according to paragraph 2, wherein the supramolecular structure is a rotaxane compound in which a number of circular molecules are penetrated by linear molecules, and both ends of the linear molecules are capped by bulky substituents.
4. The tissue-specific transporter function inhibitor according to paragraph 3, wherein the circular molecules are cyclodextrins.
5. The tissue-specific transporter function inhibitor according to paragraph 3 or 4, wherein the linear molecules are polyethyleneglycols.

6. The tissue-specific transporter function inhibitor according to any one of paragraphs 3 to 5, wherein the bulky substituents are N-benzyloxycarbonyl-L-phenylalanines.
7. The tissue-specific transporter function inhibitor according to paragraph 1, wherein the polymeric molecular structure incapable of passing through a membrane tissue is an α-cyclodextrin structure.
8. The tissue-specific transporter function inhibitor according to any one of paragraphs 1 to 7, wherein the ligand recognized by a tissue-specific transporter is an organic anionic substance, an organic cationic substance, or a peptidergic substance.
9. The tissue-specific transporter function inhibitor according to any one of paragraphs 1 to 8, wherein the tissue-specific transporter is a small intestine-specific transporter.
10. The tissue-specific transporter function inhibitor according to paragraph 9, wherein the small intestine-specific transporter is an oligopeptide transporter 1 (PEPT 1).
11. The tissue-specific transporter function inhibitor according to paragraph 10, wherein a peptidergic substance recognized by the oligopeptide transporter 1 (PEPT 1) is valyl-lysine (Val-Lys).
12. A therapeutic drug for tissue dysfunction diseases which contains the tissue-specific transporter function inhibitor according to any one of paragraphs 1 to 11 as an active ingredient.
13. A therapeutic drug for suppressing the progress of chronic renal failure which contains the tissue-specific transporter function inhibitor according to any one of paragraphs 1 to 11 as an active ingredient, wherein the inhibitor is a protein absorption inhibitor.

The invention claimed is:

1. A function-inhibitor of PEPT1 (oligopeptide transporter 1) consisting of a rotaxane compound in which a number of cyclodextrins are threaded by linear molecules, and both ends of the linear molecules are capped with bulky substituents, to which a dipeptide or tripeptide recognized by PEPT1 is bound, wherein the linear molecules are selected from the group consisting of polyethyleneglycol, polypropylene glycol, or copolymer of polyethyleneglycol and polypropylene glycol, polyamino acid, and polysaccharides, and the bulky substituents are selected from the group consisting of an oligopeptide comprising a unit or units of any one of N-benzyloxycarbonyl-L-phenylalanine, alanine, valine, leucine, isoleucine, methionine, proline, phenylalanine, tryptophan, aspartic acid, glutamic acid, glycine, serine, threonine, tyrosine, cysteine, lysine, arginine, histidine.

2. The function inhibitor of PEPT1 according to claim 1, wherein the linear molecules are polyethyleneglycols.

3. The function inhibitor of PEPT1 according to claim 1, wherein the bulky substituents are N-benzyloxycarbonyl-L-phenylalanines.

4. The function inhibitor of PEPT1 according to claim 1, wherein a dipeptide or tripeptide recognized by the oligopeptide transporter 1 (PEPT1) is valyl-lysine (Val-Lys).

* * * * *